(12) United States Patent
Wu

(10) Patent No.: US 8,492,708 B2
(45) Date of Patent: Jul. 23, 2013

(54) MULTI-DIMENSIONAL ION MOBILITY SPECTROMETRY METHODS AND APPARATUS

(75) Inventor: Ching Wu, Acton, MA (US)

(73) Assignee: Excellims Corporation, Acton, MA (US)

( * ) Notice: Subject to any disclaimer, the term of this patent is extended or adjusted under 35 U.S.C. 154(b) by 3 days.

(21) Appl. No.: 13/360,760

(22) Filed: Jan. 29, 2012

(65) Prior Publication Data

US 2012/0126109 A1  May 24, 2012

Related U.S. Application Data

(60) Division of application No. 12/471,101, filed on May 22, 2009, now Pat. No. 8,106,352, which is a continuation of application No. 11/618,430, filed on Dec. 29, 2006, now Pat. No. 7,576,321.

(60) Provisional application No. 60/766,266, filed on Jan. 5, 2006.

(51) Int. Cl.
*H01J 49/06* (2006.01)
*H01J 49/14* (2006.01)
*G01N 27/64* (2006.01)

(52) U.S. Cl.
USPC ........... 250/282; 250/288; 250/281; 250/283; 250/286; 250/287

(58) Field of Classification Search
USPC .................. 250/282, 288, 281, 283, 286, 287
See application file for complete search history.

(56) References Cited

U.S. PATENT DOCUMENTS

| | | | |
|---|---|---|---|
| 7,576,321 B2 * | 8/2009 | Wu ............................... | 250/286 |
| 8,106,352 B2 * | 1/2012 | Ching .......................... | 250/288 |
| 8,242,442 B2 * | 8/2012 | Krueger et al. ............... | 250/288 |
| 2012/0228491 A1 * | 9/2012 | Wu et al. ...................... | 250/282 |

* cited by examiner

*Primary Examiner* — Nikita Wells

(57) ABSTRACT

Various embodiments of a multi-dimensional ion mobility analyzer are disclosed that have more than one drift chamber and can acquire multi-dimensional ion mobility profiles of substances. The drift chambers of this device can, for example, be operated under independent operational conditions to separate charged particles based on their distinguishable chemical/physical properties. The first dimension drift chamber of this device can be used either as a storage device, a reaction chamber, and/or a drift chamber according to the operational mode of the analyzer. Also presented are various methods of operating an ion mobility spectrometer including, but not limited to, a continuous first dimension ionization methods that can enable ionization of all chemical components in the sample regardless their charge affinity.

6 Claims, 14 Drawing Sheets

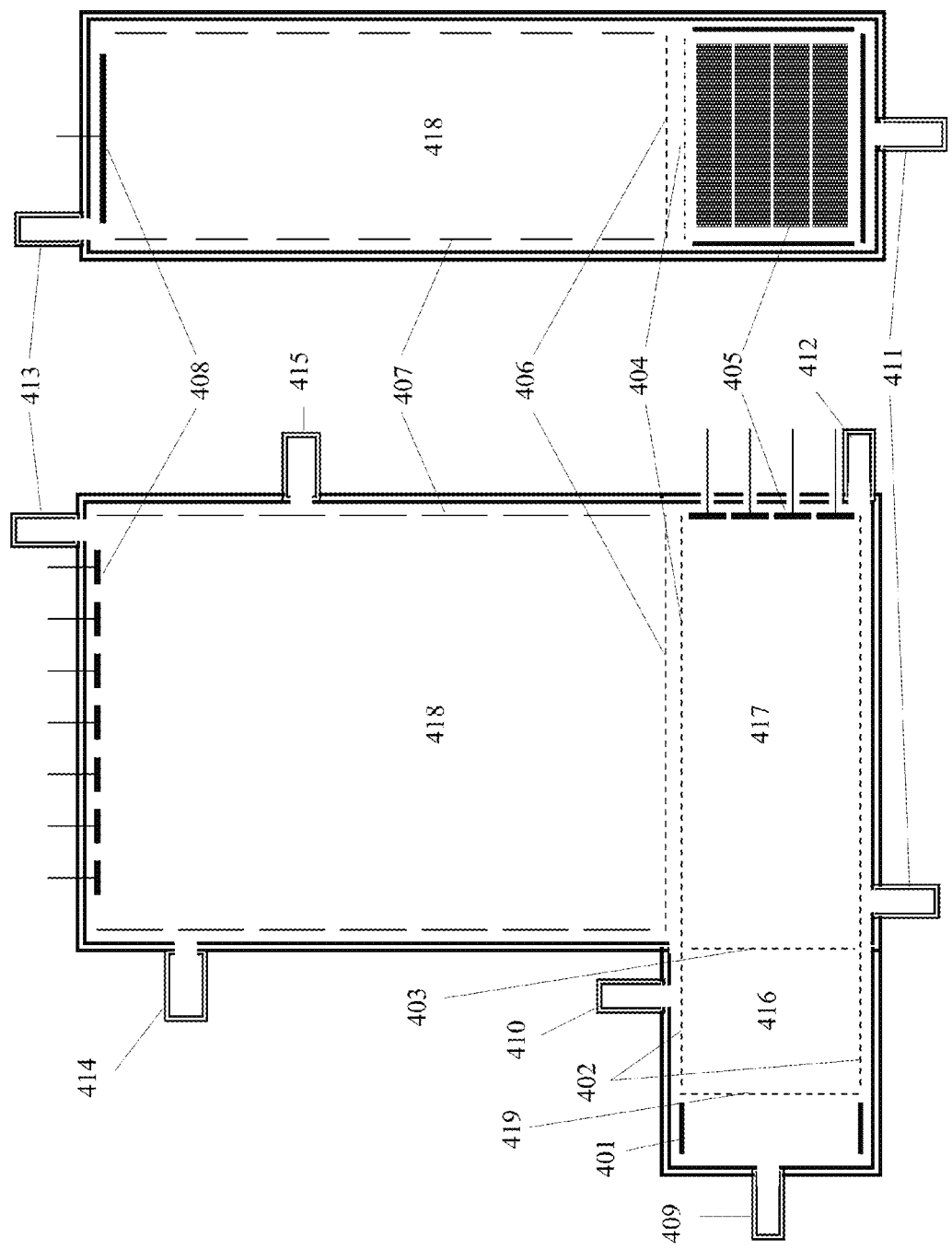

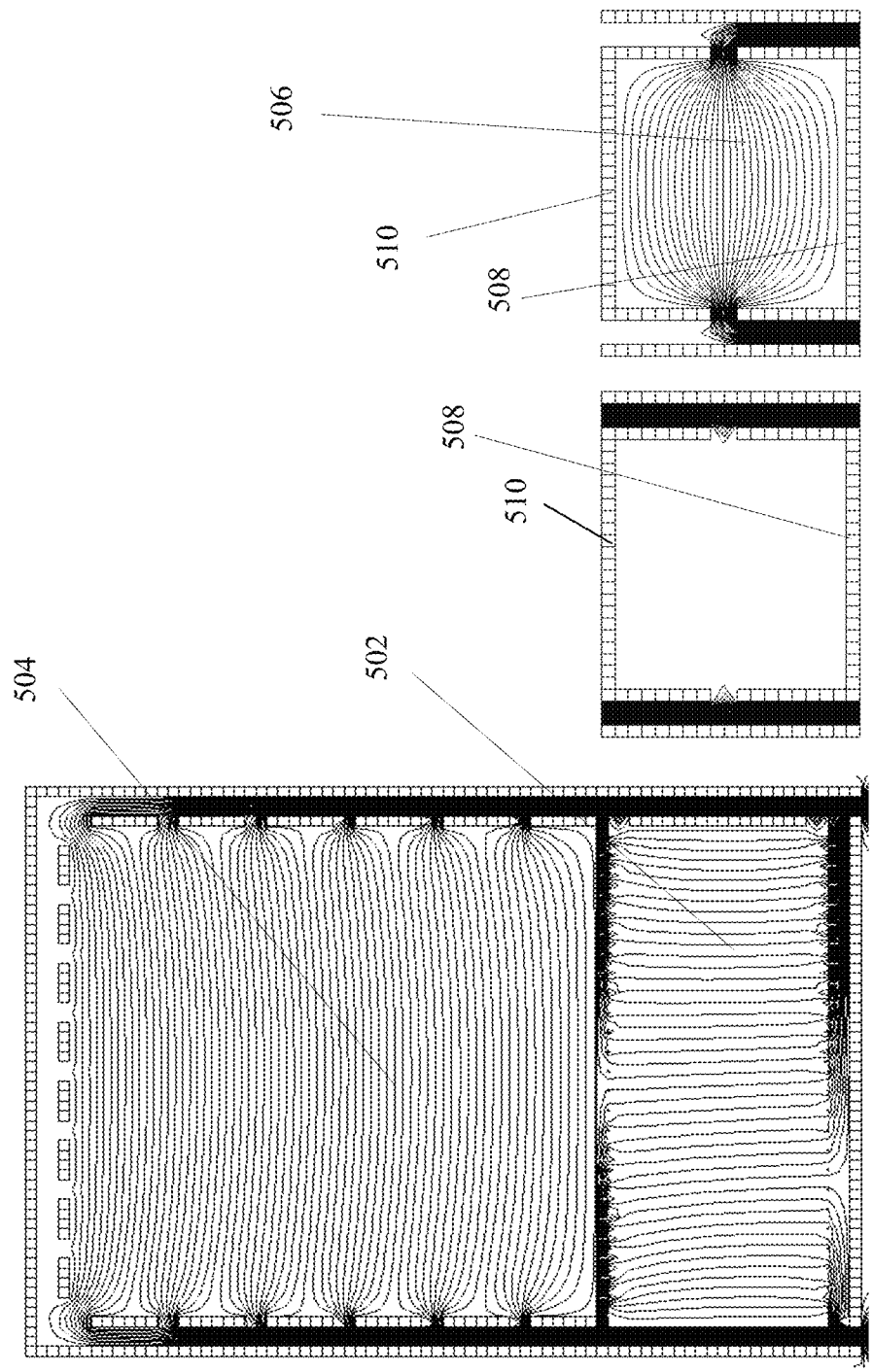

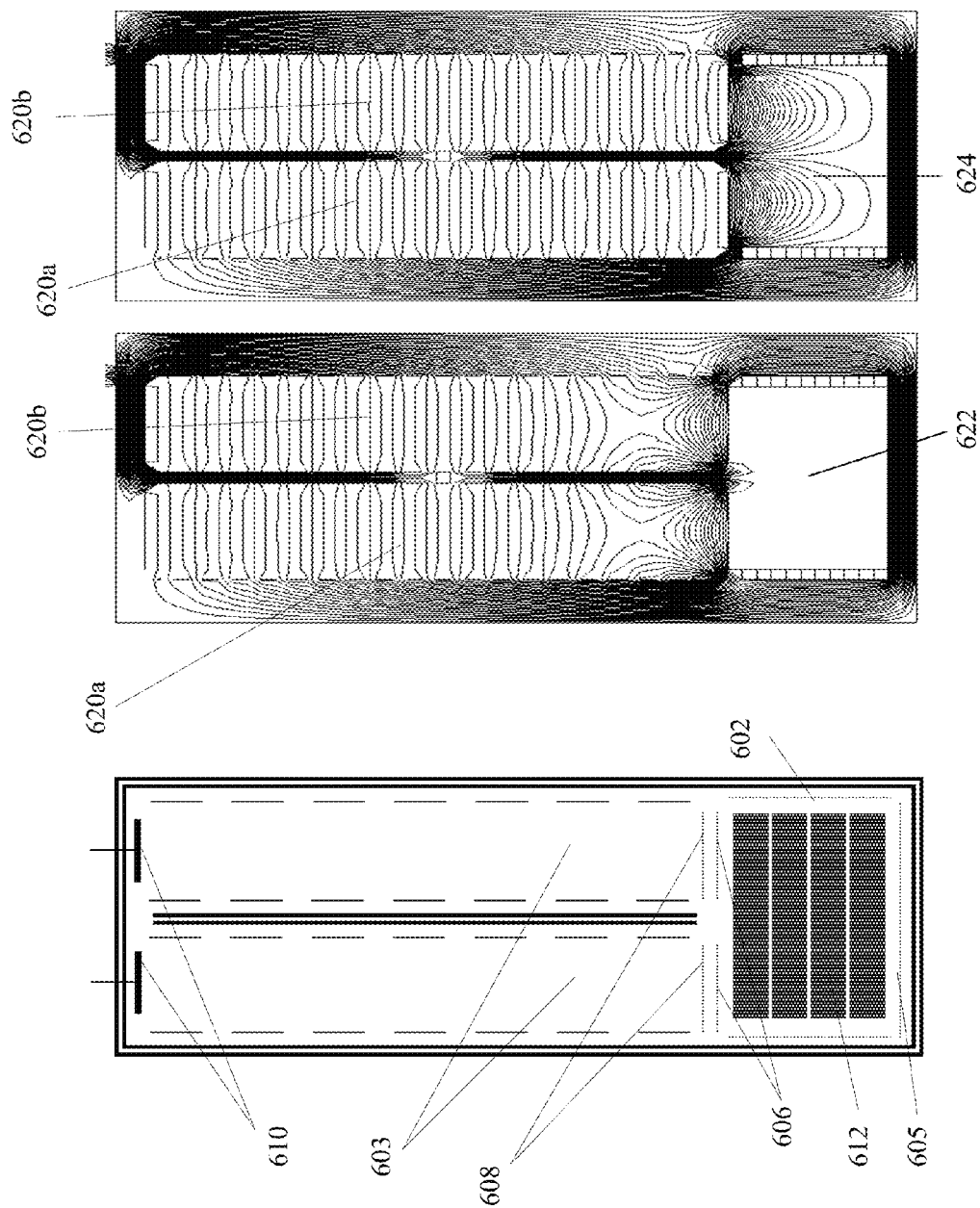

MULTI-DIMENSIONAL ION MOBILITY SPECTROMETRY METHODS AND APPARATUS

CROSS-REFERENCE TO RELATED APPLICATIONS

This is a division of application Ser. No. 12/471,101, filed May 22, 2009, now granted, which is a continuation of U.S. patent application Ser. No. 11/618,430, filed Dec. 29, 2006, the latter now issued as U.S. Pat. No. 7,576,321, which claims priority from Provisional Application 60/766,266, filed Jan. 2, 2006. The contents of all of these patent applications are incorporated herein by reference.

BACKGROUND OF THE INVENTION

Since it was invented in the early 1970's, ion mobility spectrometry (IMS) has been developed into a powerful analytical tool used in a variety of applications. There are three major forms of this instrument including independent chemical detection systems, chromatographic detectors, or hyphenated IMS mass spectrometry (MS) systems. As an independent detection system, IMS qualitatively and quantitatively detects substances in different forms relying on its capability to ionize the target substance, to separate the target substance from background based on interactions with a drift gas (i.e. a carrier gas), and to detect the substance in its ionized form. As a chromatographic detector, IMS acquires multiple ion mobility spectra of chromatographically separated substances. In combined IMS-MS systems, IMS is used as a separation method to isolate target substances before mass analysis. However, the resolution of IMS is generally consider low, often regulating such devices to qualitative use or use in environments with low levels of interferants with respect to the substances of interest.

The basic common components of an IMS system consist of an ionization source, a drift tube that includes a reaction region, an ion shutter grid, a drift region, and an ion detector. In gas phase analysis the sample to be analyzed is introduced into the reaction region by an inert carrier gas, ionization of the sample is often completed by passing the sample through a reaction region and/or a radioactive 63Ni source. The ions that are formed are directed toward the drift region by an electric field applied to drift rings that establish the drift region, and a narrow pulse of ions is then injected into, and/or allowed to enter, the drift region via an ion shutter grid. Once in the drift region, ions of the sample are separated based upon their ion mobilities and there arrival time at a detector is an indication of ion mobility which can be related to ion mass. However, it is to be understood that ion mobility is not only related to ion mass, but rather is fundamentally related to the ion-drift gas interaction potential which is not solely dependent on ion mass.

One of the major applications of IMS is to detect trace amounts of contraband chemicals. The trace detection system has been widely used in current security systems for explosive and chemical agent detections. Typically, the process starts when a security officer wipes a swab over a sampling surface, and then inserts the swab into a thermal desorber where traces of organic compounds are evaporated and introduced to the IMS. In most of these applications fast and accurate identification of contraband chemicals is essential to the security inspection mission. Portable yet high performance detection systems continue to be sought after and are highly desirable.

SUMMARY OF THE INVENTION

The present invention relates to various aspects of Multi-Dimensional Ion Mobility Spectrometry (MDIMS) methods and apparatus. In various embodiments, the MDIMS of the present inventions differentiate themselves from conventional ion mobility spectrometry (IMS) by innovatively integrating multiple ion mobility based separation steps in one device. In various embodiments, the present invention provides higher resolution and higher sensitivity than conventional IMS devices and operational approaches.

Various embodiments of the present invention provide an integrated multiple dimensional time-of-flight ion mobility spectrometric system that ionizes, separates, and detects chemical species based on their ion mobilities. These systems generally include: (a) at least one ionization source, (b) at least two drift regions, and (c) at least one ion detection device. In various embodiments, these systems separate ions in one drift dimension under one set of drift conditions; and subsequently, the separated ions are introduced into a higher dimension for further separation under the same or a different set of drift conditions. In various embodiments, the separation process can be repeated for one or more additional drift dimensions. Also, in various embodiments, the first drift dimension is used as one or more of an ionization source, reaction region or desolvation region, and drift region for the system. For example, in various embodiments, the electric field in the first drift dimension (first drift tube) can be used as a desolvation region for charged droplets.

The devices and methods of the present inventions make use of "drift tubes." The term "drift tube" is used herein in accordance with the accepted meaning of that term in the field of ion mobility spectrometry. A drift tube is a structure containing a neutral gas through which ions are moved under the influence of an electrical field. It is to be understood that a "drift tube" does not need to be in the form of a tube or cylinder. As understood in the art, a "drift tube" is not limited to the circular or elliptical cross-sections found in a cylinder, but can have any cross-sectional shape including, but not limited to, square, rectangular, circular, elliptical, semi-circular, triangular, etc.

Neutral gas is often referred to as a carrier gas, drift gas, buffer gas, etc. and these terms are considered interchangeable herein. The gas is at a pressure such that the mean free path of the ion, or ions, of interest is less than the dimensions of the drift tube. That is the gas pressure is chosen for viscous flow. Under conditions of viscous flow of a gas in a channel, conditions are such that the mean free path is very small compared with the transverse dimensions of the channel. At these pressures the flow characteristics are determined mainly by collisions between the gas molecules, i.e. the viscosity of the gas. The flow may be laminar or turbulent. It is preferred that the pressure in the drift tube is high enough that ions will travel a negligible distance, relative to the longitudinal length of the drift tube, before a steady-state ion mobility is achieved.

The axis of the drift tube along which ions move under the influence of the electrical drift field is referred to herein as a drift axis. The drift axis is often, but not necessarily, a longitudinal axis of the drift tube.

In various aspects of the present inventions, methods for operating an ion mobility spectrometer are described. In one aspect, methods of operation referred to for the sake of conciseness, and not by way of limitation, as Continuous First Dimension Ionization (CFDI) mode are described. As understood in the art, charge will preferentially be transferred from an ionized chemical species to another chemical species of higher affinity. Such charge transfer process can seriously disturb and even prevent the ionization of a chemical species of interest, and hence prevent successful analysis of that species by IMS as well as other forms of mass spectrometry. The CFDI methods of the present inventions facilitate the formation of ions of low charge affinity ions and thus, in various embodiments, can increase the sensitivity of IMS. The CFDI method also increases the dynamic response range of the IMS and provides better quantitative information when the spectrometer is used to analyze sample mixture.

In various embodiments, a CFDI method comprises pulsing a gas phase sample into a first drift tube and conveying the sample pulse by gas flow in a first direction along at least a portion of the first drift tube. As a result, the first direction is substantially parallel to the direction of carrier gas flow in the first drift tube. Pulses of counter-moving reactant ions are used to ionize chemical species in the sample pulse. The sample pulse can be introduced to the spectrometer either in the reaction region or in the drift region. In some modes of operation, the carrier gas and sample pulse can have a speed approaching to zero, but have the reactant ions moving toward sample pulse. For example, a first group of reactant ions are pulsed into the first drift tube and conveyed by the first drift tube electrical field in a second direction that is towards the sample pulse. The first group of reactant ions is preferably pulsed into the first drift tube at a predetermined time. The predetermined time can be chosen to select, at least roughly, the position in the first drift tube where the sample pulse and first group of reactant ions interact. As the first group of reactant ions interacts with the sample pulse, one or more chemical species are ionized and a first ionized chemical species is produced. Typically, the chemical species in the sample pulse with the highest charge affinity is preferentially ionized.

A second group of reactant ions is pulsed into the drift tube after the first group, also preferably at a second predetermined time, and conveyed by the electrical field of the first drift tube towards the sample pulse. The second predetermined time, which is necessarily later than that chosen for the first reactant ion group, can be chosen to select, at least roughly, the position in the first drift tube where the sample pulse and first group of reactant ions interact. In various embodiments, the second predetermined time is chosen to allow time for at least a portion of the first ionized chemical species to be extracted into a second drift tube.

As the second group of reactant ions interacts with the sample pulse, one or more chemical species are ionized and a second ionized chemical species is produced. Typically, the second chemical species ionized is the species in the sample pulse with the second highest charge affinity. The process can be repeated, e.g., providing a third group of reactant ions to produced a third ionized chemical species, a further group of reactant ions to produced a fourth ionized chemical species, etc. as the operator desires, to ionize a chemical species of interest.

In various embodiments, at least a portion of the first ionized chemical species in the first drift tube is extracted into a second drift tube by generating an electrical field over at least a portion of the first drift tube that moves the ions into the second drift tube. This electrical field is often referred to herein as a "kick-out" pulse or "kick-out" field as it removes the ions from the first drift tubes. Preferably, the kick-out field is applied to a portion of the first drift tube that is substantially free of reactant ions, by selecting, for example, the timing, spatial extent, or both at which field is applied. For example, in various embodiments, the kick-out field is applied prior to the ionization of a second chemical species by the second group of reactant ions.

In various embodiments, a kick-out field is applied to extract a nth ionized chemical species prior to formation of the next, (n+1)th, ionized chemical species. In various embodiments, a kick-out field is applied to extract two or more ionized chemical species at substantially the same time. In various embodiments, a combination of selective ionized chemical species extraction and multiple ionized chemical species extraction is performed.

Accordingly, in various embodiments, a CFDI method of the present inventions comprises: (a) pulsing a gas phase sample into a first drift tube at a first time; (b) conveying the gas phase sample pulse in a first direction along at least a portion of the first drift tube, wherein the first direction is substantially parallel to the direction of carrier gas flow in the first drift tube; (c) providing a plurality of pulses of reactant ions into the first drift tube at predetermined times relative to the first time; (d) conveying by an electrical field the pulses of reactant ions in a second direction along at least a portion of the first drift tube, wherein the second direction is substantially anti-parallel to the direction of carrier gas flow in the first drift tube; (e) interacting a group of reactant ions, comprising one or more of the plurality of pulses of reactant ions, with the gas phase sample pulse to ionize a chemical species in the gas phase sample pulse; and (f) repeating the step of interacting a group of reactant ions with the gas phase sample pulse until all chemical species of interest are ionized, wherein chemical species of different charge affinity are ionized at different positions along the first direction.

In various embodiments, the methods comprise extracting at least a portion of the ionized chemical species in the first drift tube into a second drift tube by generating at one or more predetermined extraction times an electrical field over at least a portion of the first drift tube, the second drift tube having a longitudinal axis which is substantially parallel or perpendicular to a longitudinal axis of the first drift tube. Preferably, the one or more predetermined extraction times are selected such that ionized chemical species are extracted in a time interval during which the portion of the first drift tube from which ionized chemical species are extracted is substantially free of reactant ions.

In various embodiments, a CFDI method of the present inventions use a second drift tube; preferably the second drift tube has a longitudinal axis which is substantially perpendicular to a longitudinal axis of the first drift tube. In various embodiments, ionized chemical species extracted into the second drift tube are directed towards an ion detector and are characterized by their arrival time at the ion detector based at least on their mobility under the conditions of the second drift tube.

Preferably, the ratio of the electrical field strength to the gas number density (E/N value) is substantially constant in the first drift tube, the second drift tube, or both. Preferably the electrical field strength is substantially constant in the first drift tube, the second drift tube, or both. It is to be understood, however, that the conditions in the first and second drift tubes can be different. For example, in various embodiments, one or more of the carrier gas, carrier gas density, carrier gas flow rate, electrical field strength, and temperature, are different in the first and second drift tubes.

In various embodiments, the CFDI methods of the present inventions have a variety of practical applications. For example, a continuous first dimension ionization method of operation of a MDIMS could be used to facilitate overcoming a fundamental shortcoming of conventional IMS, i.e., charge competition in the ionization source and/or reaction region of the spectrometer, thus in various embodiments offering an ionization opportunity for substances with very different charge affinities. Various embodiments of the CFDI methods could be used, e.g., to isolate charged substances and prevent them from losing charges to other co-existing substances; and thus facilitate increasing system sensitivity to the substances of interest.

In various aspects, the present invention provides an ion mobility spectrometer comprising three drift tubes and methods for such apparatus. In one aspect, provided are methods of operation referred to for the sake of conciseness, and not by way of limitation, as Dual Polarity Ion Extraction (DPIE) methods.

In various embodiments, the present inventions provide a multi-dimensional ion mobility spectrometer that comprises three drift tubes, a first drift tube for performing a first dimension of IMS, ion formation (e.g., by CFDI), or both, and two additional drift tubes (a second and third drift tube) for performing a second dimension of IMS. In various embodiments, the second and third drift tubes are configured and operated to perform a second dimension of IMS on different polarities of ions; IMS under different drift tube conditions, or both. Examples of various embodiments of such MDIMS of the present inventions are schematically illustrated, for example, in FIGS. 1, and 6-9. For the sake of conciseness, and not by way of limitation, we refer to such ion mobility spectrometer systems as Dual Second Dimension Ion Mobility Spectrometers (DSDIMS).

Accordingly, in various embodiments, the present invention provide an ion mobility spectrometer that comprises: (a) a first drift tube having a first drift axis; (b) a second drift tube having a second drift axis substantially perpendicular to the first drift axis and an inlet in fluid communication with the first drift tube; (c) a third drift tube having a third drift axis substantially parallel to the second drift axis and substantially perpendicular to the first drift axis, and having an inlet in fluid communication with the first drift tube; (d) an electrode arranged opposite the inlet of the second drift tube; and (e) an electrode arranged opposite the inlet of the third drift tube.

The second and third drift tubes can be arranged in a variety of ways. In various embodiments, the second drift tube and third drift tube are arranged substantially opposite each other across from the first drift tube. An example of such embodiments includes, but is not limited to, the embodiments schematically illustrated in FIG. 8. The opposed arrangement of the second and third drift tubes can provide structures where the electrode arranged opposite to the inlet of the second drift tube comprises the inlet to the third drift tube; and the electrode arranged opposite the inlet of the third drift tube comprises the inlet to the second drift tube.

In various embodiments, the second drift tube and third drift tube are arranged substantially side-by-side. Examples of such embodiments include, but are not limited to, the embodiments schematically illustrated in FIGS. 1, 6, 7, and 9. In various embodiments, the proximity of the second and third drift tubes leads to a preferred embodiments where the electrode arranged opposite to the inlet of the second drift tube is the same structure as the electrode arranged opposite to the inlet of the third drift tube. For example, in various embodiments, an electrical potential V is applied to this electrode and a lower electrical potential is applied to the inlet of the second drift tube. A higher potential is applied to the inlet of the third drift tube in order to attract ions of different polarity to the second and third drift tubes.

The Dual Second Dimension Ion Mobility Spectrometers (DSDIMS) of the present invention can include higher dimensions of IMS. In various embodiments, a DSDIMS of the present invention also comprises (a) a fourth drift tube having an inlet in fluid communication with the second drift tube and having a fourth drift axis substantially perpendicular to the second drift axis; and (b) a fifth drift tube having an inlet in fluid communication with the third drift tube and having a fifth drift axis substantially perpendicular to the third drift axis. An example of such embodiments includes, but is not limited to, the embodiments schematically illustrated in FIG. 1. In various embodiments, the fourth drift axis and the fifth drift axis are both substantially perpendicular to the first drift axis.

A wide variety of ion source and ion detector configurations are contemplated for the multi-dimensional IMS systems of the present inventions. For example, in various embodiments, a DSDIMS of the present inventions also comprises an ion source in fluid communication with a first end of the first drift tube and an ion detector located at an end of the first drift tube opposite the first end. An example of such embodiments includes, but is not limited to, the embodiments schematically illustrated in FIG. 1.

In various embodiments, a DSDIMS of the present inventions also comprises a first ion source in fluid communication with a first end of the first drift tube; and a second ion source in fluid communication with an end of the first drift tube opposite to the first end. An example of such embodiments includes, but is not limited to, the embodiments schematically illustrated in FIG. 7.

In various embodiments, a DSDIMS of the present inventions also comprises an ion source positioned between the inlet to the second drift tube and the inlet to the third drift tube. The ion source is in fluid communication with the first drift tube; and a first ion detector located at a first end of the first drift tube. In various embodiments a second ion detector is located at an end of the first drift tube opposite to the first end. An example of such embodiments includes, but is not limited to, the embodiments schematically illustrated in FIG. 9.

In various aspects, the present inventions provide methods for operating a DSDIMS. In one aspect, provided are methods of operation referred to for the sake of conciseness, and not by way of limitation, as Dual Polarity Ion Extraction (DPIE). In various embodiments, a MDIMS of the present inventions, including DSDIMS, can be operated to include ion storage. For example, in various embodiments, loss of ions in ionization and drift chambers suffered by conventional IMS designs can be reduced or avoided. For example, a MDIMS operated in DPIE mode can provide substantially simultaneous analysis of positive and negative ions, e.g., such as would be present in peroxide- and nitro-based explosives detection. Such operation can, in various embodiments, provide increased sensitivity over conventional IMS approaches. In various embodiments, a DSDIMS configuration of the present inventions could be provided in very compact format, suitable for hand-held instrumentation. Such hand-held devices could find widespread use in the area of homeland security.

Accordingly, in various embodiments, the present invention provides methods for operating an ion mobility spectrometer, such as, e.g., a DSDIMS, where the ion mobility spectrometer comprises (a) a first drift tube having a first drift axis; (b) a second drift tube having a second drift axis substantially perpendicular to the first drift axis; (c) a third drift tube having a third drift axis substantially parallel to the second drift axis and substantially perpendicular to the first drift axis; (d) a first electrode arranged opposite the inlet of the second drift tube; and (e) a second electrode arranged opposite the inlet of the third drift tube.

The methods in various embodiments, comprise the steps of: (a) providing a gas sample comprising positive ion chemical species and negative ion chemical species to the first drift tube; (b) spatially separating along the first drift axis one or more of the chemical species by collisions with a first carrier gas in the first drift tube; (c) applying an electrical potential difference between the first electrode arranged opposite to the inlet of the third drift tube in order to move at least a portion of the positive ion chemical species into the second drift tube and substantially simultaneously move at least a portion of the negative ion chemical species into the third drift tube; (d) spatially separating along the second drift axis one or more of the positive ion chemical species by collisions with a second carrier gas in the second drift tube and conveying at least a portion of the separated positive ion chemical species to an ion detector; and (e) spatially separating along the third drift axis one or more of the negative ion chemical species by collisions with a third carrier gas in the third drift tube and conveying at least a portion of the separated negative ion chemical species to an ion detector.

The methods can be used, for example to determine the presence or absence of one or more chemical species in a sample, such as for example, chemical species associated with peroxide-based explosives and nitro-based explosives, in a single measurement. Such determinations can be made, based on the arrival time at the ion detector associated with the second drift, the third drift tube, or both.

The drift conditions in the first second and third drift tubes can be substantially the same or different. For example, in various embodiments, one or more of the drift tube conditions of carrier gas, carrier gas density, carrier gas flow rate, electrical field strength, and temperature, are different between one or more of the first drift tube, the second drift tube, and the third drift tube.

In various embodiments, the use of different drift conditions is one aspect of various methods of the present inventions. For example, for the same sample, various embodiments of the present inventions provide means of achieving multiple ion mobility based separations under different conditions in one data acquisition cycle. Conditions including the type of drift gas, temperature, pressure, electric field strength, flow rate, etc. These conditions can be adjusted to change ion mobility based separation characteristics of individual substances. Thus, in various embodiments, substances irresolvable in a conventional IMS can be separated in the MDIMS; preferably in one data acquisition cycle.

In various embodiments, the present invention provides methods for operating an ion mobility spectrometer, such as, e.g., a DSDIMS, where the ion mobility spectrometer comprises: (a) a first drift tube having a first drift axis; (b) a second drift tube having a second drift axis substantially perpendicular to the first drift axis; (c) a third drift tube having a third drift axis substantially parallel to the second drift axis and substantially perpendicular to the first drift axis; (d) a first electrode arranged opposite the inlet of the second drift tube; and (b) a second electrode arranged opposite the inlet of the third drift tube.

The ion mobility spectrometer is operated with different drift conditions for the second drift tube and the third drift tube. The operation comprises the steps of: (a) providing a gas sample comprising ionic chemical species to the first drift tube; (b) spatially separating along the first drift axis one or more of the chemical species by collisions with a first carrier gas in the first drift tube under a first set of drift conditions; (c) applying an electrical potential difference between the first electrode arranged opposite to the inlet of the third drift tube in order to move at least a portion of the ionic chemical species into the second drift tube and substantially simultaneously move at least a portion of the ionic chemical species into the third drift tube; (d) spatially separating along the second drift axis one or more of the ionic chemical species by collisions with a second carrier gas in the second drift tube under a second set of drift conditions and conveying at least a portion of the separated ionic chemical species to an ion detector; and (e) spatially separating along the third drift axis one or more of the negative ion chemical species by collisions with a third carrier gas in the third drift tube under a third set of drift conditions and conveying at least a portion of the separated ionic chemical species to an ion detector; wherein the second and third sets of drift conditions are different.

In various aspects, the present inventions provide multi-dimensional ion mobility spectrometric systems comprising three or more dimensions of IMS. In various embodiments, a MDIMS comprises: (a) an ion source in fluid communication with a first drift tube, the first drift tube having a first drift axis; (b) a second drift tube having a second drift axis substantially perpendicular to the first drift axis; (c) a third drift tube having a third drift axis substantially perpendicular to the second drift axis; and (d) a first ion detector in fluid communication with the third drift tube. In various embodiments, the third drift axis is substantially perpendicular to both the second drift axis and the first drift axis.

In various aspects, the present inventions provide methods of operating multi-dimensional IMS systems comprising two or more dimensions of IMS. It is to be understood, for example, that the methods of CFDI can be used with any of the embodiments of a IMS of the present inventions comprising a first drift tube (dimension). It is to be understood, for example, that in any of the embodiments of the present inventions that the first drift tube (dimension) can be used as one or more of an ionization source, reaction region or desolvation region, and drift region for the system. It is also to be understood that the methods of the present inventions can include a step of adding compound to one or more of the drift dimensions, the compound facilitating the separation of chiral chemical species.

It is believed that various embodiments of the present inventions can be valuable tools and methods in the detection of trace compounds. By way of example, and not by way of limitation, it is believed that various embodiments of the present inventions could provide one or more of improved resolution and improved sensitivity in comparison with conventional single dimension IMS systems.

For example with respect to resolution, the resolving power that can be achieved in various embodiments of the multi-dimensional systems of the present inventions is predicted to be between about 80 and 100. Compared to the resolving power of 10-30 offered by conventional commercially available trace detectors, various embodiments the present inventions could theoretically in practice resolve 63 more chemicals in an ion mobility spectrum than these conventional IMS systems. For example, assuming in a commercial system a TNT drift time of 10 ms, and a half height peak width of 0.5 ms, then the conventional system would have a resolving power ($R=t/w1/2$) of 20 and peak capacity of 2 peaks/ms. If a useable drift time range in a mobility spectrometer was 9 ms, the system could theoretically distinguish 18 compounds in a single mobility spectrum. In comparison, a system with a resolving power of 90, total number of peaks that theoretically can be distinguished is 81. Such an improvement could theoretically allow the higher resolving system to separate interferants from targeted explosives; thus, e.g., reducing the false alarm rate in contaminated operational environments.

For example with respect to sensitivity, various embodiments of the present inventions provide a unique multi-dimensional scheme which can facilitate improving ion transportation efficiency inside the spectrometer and, consequently, improving system sensitivity. With improved resolving power, detection thresholds can be set lower. In various embodiments, the system sensitivity of a MDIMS system of the present inventions can be in sub-nanogram range under targeted operating environment (not only laboratory conditions).

In various aspects, the present invention provides multi-dimensional IMS based detection systems in compact size. Instruments of the present inventions can, in various embodiments, be used as portable trace detection systems for detection of chemicals, for example, for detection of explosive materials as may be useful in transpiration security or other uses. Preferably, the new detection systems of the present inventions have the same or similar operational controls and incorporate a user interface similar to current systems. In various preferred embodiments, a compact high performance trace detection system is provided which can answer the challenges of performing explosive trace detection missions in complex environments including maritime/industrial environments.

For example, various embodiments of the present inventions can provide an MDIMS that offers trace detection in compact size with performance comparable with or better than certain conventional desktop units, e.g. a Smith 500DT, which is manufactured and available from Smiths Detection. The compact instrument embodiment designs reduce total weight of the system and power consumption. One specific embodiment of a compact design (or hand-held) MDIMS according to the present invention has a size that is approximately 12 w×8 h×4 d inches and a weight that is under 12 pounds and in some embodiments significantly under 10 pounds.

Various embodiments of the present inventions include an ion detector. A wide variety of ion detectors are suitable for use in the present inventions including, but not limited to, to Faraday plates, electron multipliers, photo-multipliers, charge to photon conversion devices, charge-coupled devices (CCD), etc. It is to be understood that wherever use is made of an ion detector in the present inventions, an ion detector system can be used instead; where an ion detector system in this context comprises an ion detector and a mass spectrometer disposed between the ion detector and an IMS dimension of the present inventions. Suitable mass spectrometers for this purpose include, but are not limited to, time-of-flight (TOF) and RF multipole mass spectrometers.

In another aspect, provided are articles of manufacture where the functionality of a method of the invention is embedded on a computer-readable medium, such as, but not limited to, a floppy disk, a hard disk, an optical disk, a magnetic tape, a PROM, an EPROM, CD-ROM, DVD-ROM, or resident in computer or processor memory. The functionality of the method can be embedded on the computer-readable medium in any number of computer readable instructions, or languages such as, for example; FORTRAN, PASCAL, C, C++, BASIC and, assembly language. Further, the computer-readable instructions can, for example, be written in a script, macro, or functionally embedded in commercially available software, (e.g. EXCEL or VISUAL BASIC).

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

BRIEF DESCRIPTION OF THE DRAWINGS

FIGS. 4A and 4B are schematic drawings of various embodiments of a multi-dimensional ion mobility spectrometer of the present inventions having two perpendicular electric field regions, where FIG. 4A depicts a front cross-sectional view and FIG. 4B depicts a side cross-sectional view of the MDIMS.

FIGS. 5A-C show a simulation of the electric field distribution in the MDIMS of FIGS. 4A-4B. FIG. 5A depicts drift electric field in the first and second drift region of both dimensions. FIG. 5B is a side cross-sectional view of the first dimension electric field during mobility measurement in the first dimension. FIG. 5C depicts a side cross-sectional view of the first dimension electric field distribution when a "kick out" voltage is applied to bring the ions into the second dimension. FIG. 6A is schematic drawing of various embodiments of a SDSIMS. In various embodiments, positive and negative ions in the first dimension can be extracted into two separate drift regions of a second dimension 603 and positive and negative ions can thus be measured substantially simultaneously. FIGS. 6B and 6C are simulation results of electric fields distribution in the first dimension 622 and 624 and the second dimension 620$a$ and 620$b$. FIG. 6B depicts the electrical fields 622 before and/or after a "kick out" pulse is applied. FIG. 6C depicts the fields 624 during the application of a "kick out" pulse.

FIGS. 12A and 12B provide schematic two-dimensional cross sectional views and FIG. 12C provides a schematic three-dimensional cross-sectional view.

DETAILED DESCRIPTION OF VARIOUS EMBODIMENTS

In various aspects, the present invention provides multi-dimensional ion mobility spectrometry (MDIMS) systems, preferably with multi-dimensional electric field designs in one integrated spectrometer, and methods of operating such systems. In various embodiments, the MDIMS systems and/or methods provide improved sensitivity and resolution compared to conventional single dimension drift tubes. In various embodiments, improved sensitivity can be achieved by using the first dimension as an ion storage region to improve system duty cycle. In various embodiments the MDIMS systems and/or methods provide improved mobility resolution. In various embodiments, improvements can be achieved by the use of drift regions which can further separate ions that are or have already been separated based on their mobilities. In various embodiments, as ion species are being separated in the first dimension, the columbic repulsion among them is reduced by transferring them to a second IMS dimension (e.g., using a kickout pulse). Thus, in various embodiments, higher mobility resolution can be experienced in the second dimension. In various embodiments, the first dimension can be used as an ion reaction region where further ion conversion can be achieved. In various embodiments of a MDIMS, and appropriate electric field application, a MDIMS can be used to detect both positive and negative ions substantially simultaneously.

Prior to further describing various detailed embodiments of the present inventions, it may be helpful to a fuller understanding thereof to discuss various embodiments of the apparatus and methods of the present inventions in the context of one embodiment of a three dimensional MDIMS device.

Figure 1:
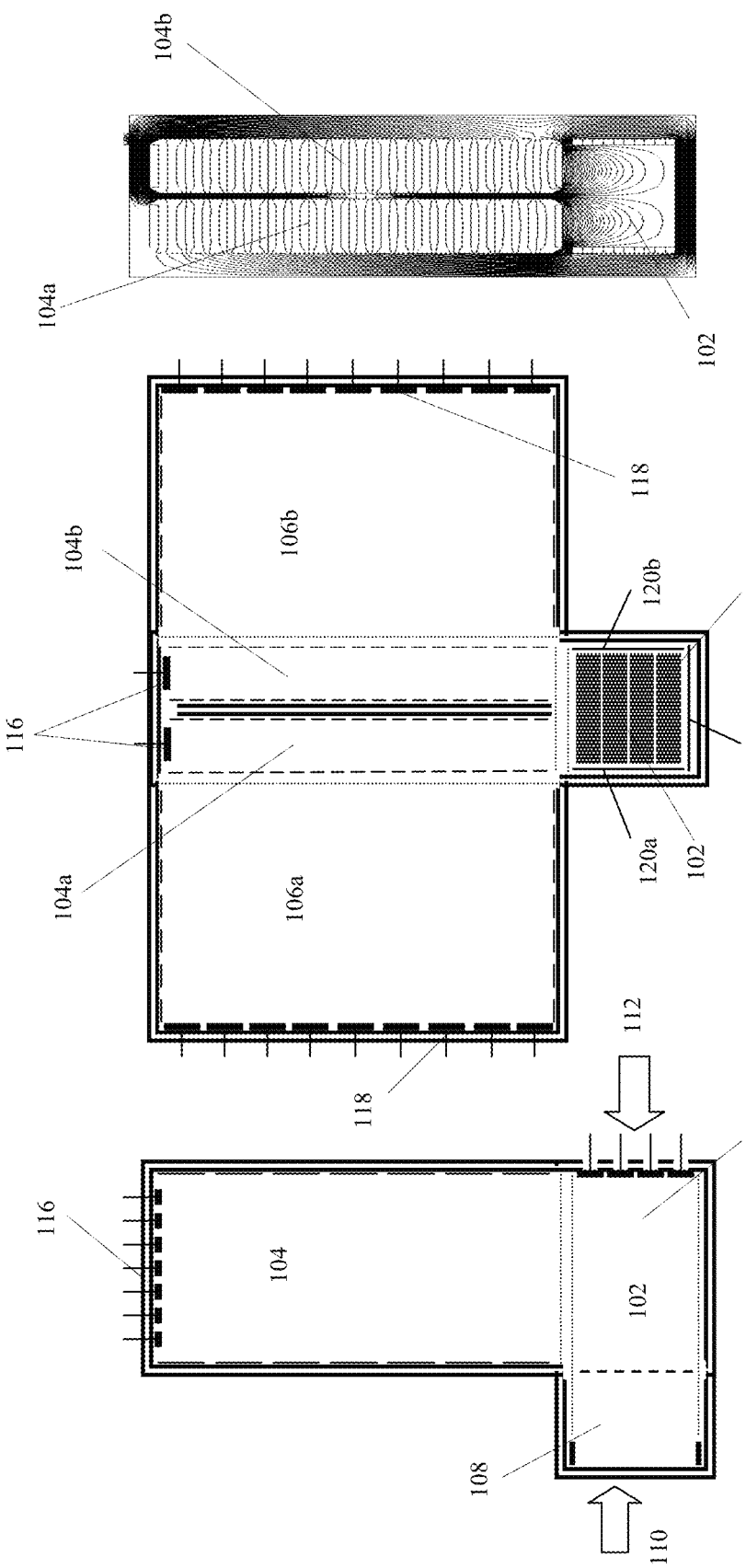
FIGS. 1A and 1B schematically shows cross-sectional views of an embodiment of a three dimensional multi-dimensional ion mobility spectrometer (MDIMS) device of the present inventions.
FIG. 1C shows simulated electrical potential lines within the first and second dimensions of IMS during a "kick-out" of ions from the first to second dimension. The second dimension can be used for, for example, single and/or dual polarity mode operation.

FIGS. 1A-1C illustrate various embodiments of a three dimensional MDIMS system. FIG. 1A is a side view of a first dimension drift region 102 and a second dimension drift region 104. FIG. 1B shows a side-view of the second dimension drift region 104 and a third dimension drift region 106. In FIGS. 1A-1C, the second dimension comprises two drift tubes 104a, 104b, and there is a separate third dimension drift tube 106a, 106b associated with each of the second dimension drift tubes. The second dimension 104 can be used for single or dual polarity mode operation. In various embodiments of the MDIMS, it is understood that a preferred embodiment is to arrange the drift axis of each dimension in orthogonal geometry, however, the drift axis can be arranged in parallel, anti-parallel or with an angle in between to achieve similar results.

It is to be understood, that the electrical drift field strength-to-gas number density ratio (E/N value, often expressed in units of Townsend) in all IMS dimensions of the present MDIMS apparatus and methods is chosen to establish a steady-state drift environment, sometimes referred to as a low field environment.

With the MDIMS of the present inventions, the ion mobility spectrum can be represented, e.g., in a 2-D or 3-D plot, and can use a non-linear detection window. Chemicals can be identified in their 1-D, 2-D or 3-D mobility profile. This mobility profiling method can provide additional information and thus, can provide greater confidence for chemical (e.g., explosive) identification.

In various embodiments a DPIE operational mode can be conducted using the first dimension 102 as a flow through cell where both positive and negative ions are brought into the first drift chamber by gas flow while the drift voltage in the first dimension is turned off (i.e., substantially no drift field is present). At a predetermined time ions are and kicked out into the second dimension, preferably such that the positive and negative ions in the first dimension are substantially simultaneously extracted into two separated drift chambers 104a, 104b in the second dimension 104. After ions are separated in the second dimension 104, they can be further separated and detected in the third 106 or higher dimensions.

In various embodiments, ionized samples are guided into and/or formed in the first drift region 102 and subject to a first order separation based on mobility (resembling conventional IMS). At a given predetermined time, separated ions in the first dimension (first drift tube) are kicked out into the second drift dimension 104 drift region where they are separated in the direction that is substantially perpendicular to the first drift direction. The same process can be continued in the higher dimensions if desired with further dimensions of IMS.

FIG. 1C shows simulation results of the electric field distribution of a DPIE process in a DSDIMS of FIGS. 1A and 1B. In FIG. 1C, the three walls in the first dimension 102 (left, bottom, and right) are at 1,000 V and the gate grids are set at 0 V and 2,000 V respectively. The equi-potential lines are shown in the figure. The sample gas flow used to carry ions through the first dimension can be exhaust, e.g., behind the first dimension detector 114. After ions are separated in the second dimension 104, a kick out voltage can be applied to bring the separated ions into the third dimension 106. In a continuous sample detection scenario, the sequence will repeat. For a chemical mixture that may form both positive and negative ions, various embodiments of the DPIE technique can extract more than 50% of both positive and negative ions into the second dimension.

In various embodiments, the MDIMS devices can transport ions between each dimension without significantly losing resolving power. Referring to FIG. 11, in various embodiments, when ions are separated in the first dimension; they can look like a thin plate 1110. To move them into the direction that is perpendicular to the first dimension, voltages are changed on the appropriate electrodes (typically an electrode opposite the inlet, the inlet itself, or both) within a microsecond range. The electric field during these kick out moments can be manipulated to create temporary high and low electric field zones. The thin plate 1110 in the high field zone can be compressed into a thin line 1120 in the low field zone of the second dimension.

One area of application of the present inventions is in the detection of trace amounts of chemicals, such as is often required in security applications, such as drug and explosive screening. In practice such tasks can be difficult to perform for a variety of reasons.

For example, detecting trace explosives in a highly contaminated environment poses great challenges to current IMS-based trace detection systems. The contamination can either cause false positive or false negative indications. A few common phenomena observed in commercially available IMS systems that can lead to these problems are:

1. Overlapping or adjacent peaks in the explosive detection window from chemicals that have similar ion mobilities as targeted explosives, that can cause false positives;
2. Undefined ion mobility peak shifting through explosives detection window that can cause false positives; and
3. High chemical background noise from contaminants can cause false negatives of explosive detection;

Various embodiments of the systems and methods of the present invention can facilitate overcoming these problems in trace chemical detection.

Figure 2:
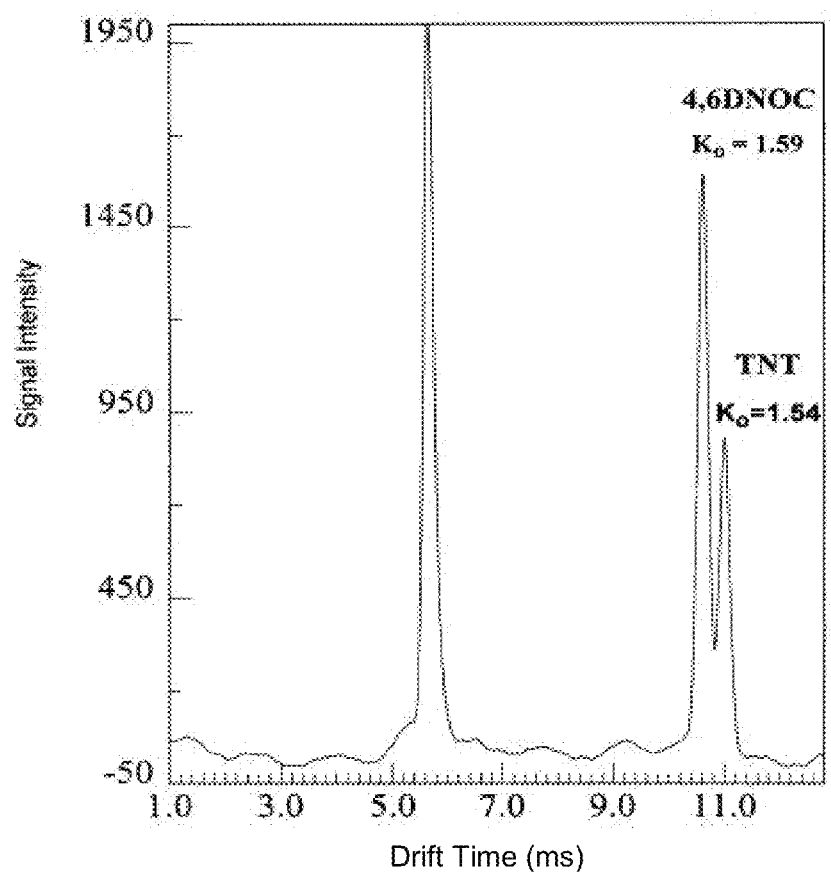
FIG. 2 is an ion mobility spectrum showing the resolution of TNT from 4,6-dinitro-o-cresol (4,6 DNOC), a component of acidic fog commonly found in airport environments due to jet exhaust. The spectrum was obtained with a MDIMS with a configuration according to the present invention.
Figure 3A:
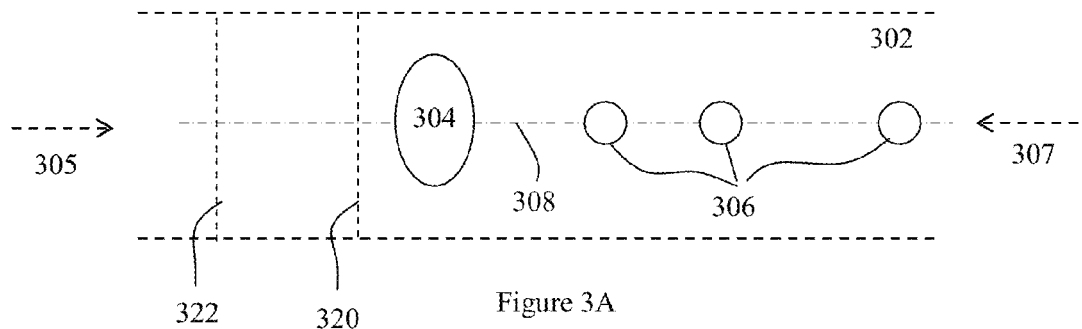
FIG. 3 schematically illustrates various concepts of a CFDI process.
Figure 3B:
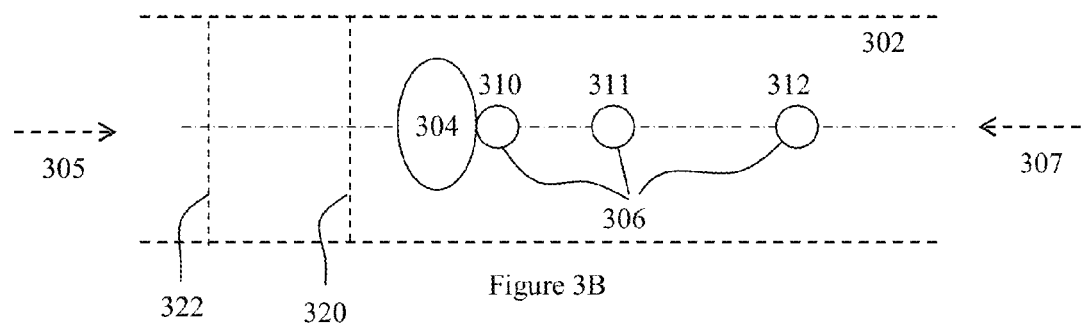
Figure 3C:
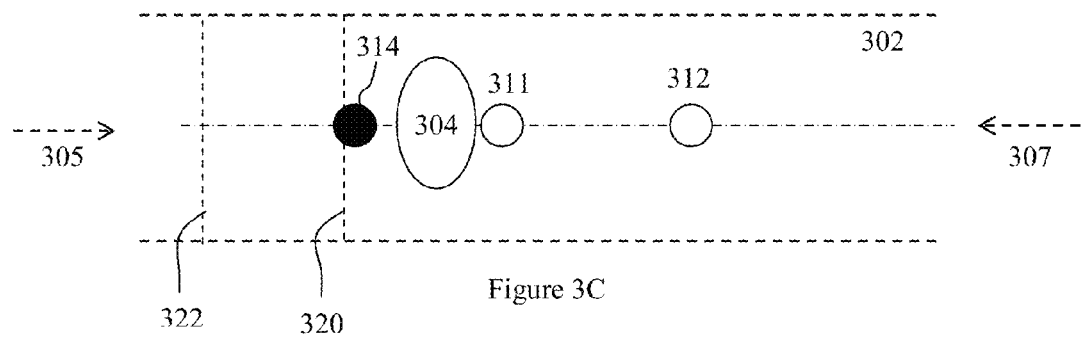
Figure 3D:
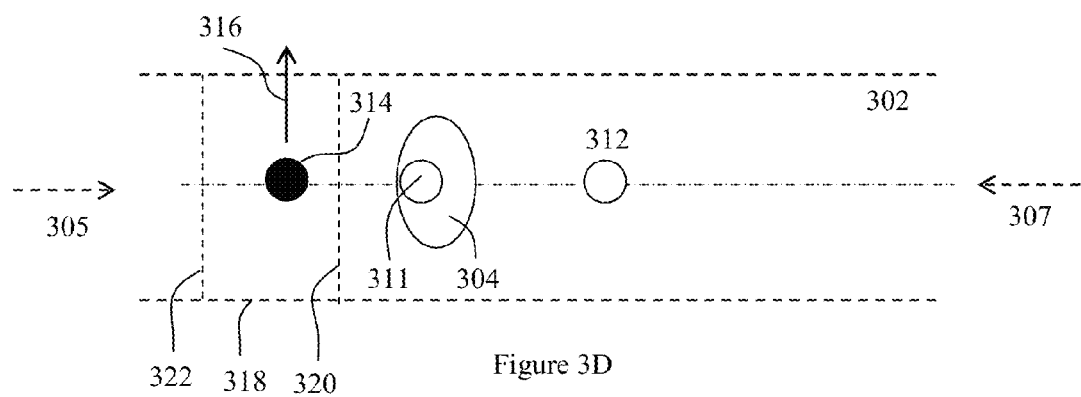

The first phenomenon mentioned above (overlapping or adjacent peaks) can be reduced using MDIMS in accordance with various embodiments of the present inventions. Examples of the performance of a high resolution IMS is illustrated in FIG. 2. FIG. 2 shows ion mobility spectra of TNT and 4,6-dinitro-o-cresol (4,6 DNOC). The compound 4,6-dinitro-o-cresol (4,6 DNOC) is a component of acidic fog commonly found in airport environments due to jet exhaust. It can be seen that even though TNT and 4,6 DNOC have very similar ion mobilities of 1.59 and 1.54, respectively, with the resolving power of about 60, they are separated and properly identified. In the MDIMS system, two high resolution drift chambers as shown in above example can be used to generate a two-dimensional mobility profile of both positive and negative ions simultaneously. The two-dimensional ion mobility data provides higher confidence in explosive detection. As a practical operational approach, first dimension mobility spectra can be acquired for higher throughput screening; when peaks are detected in the explosive detection window from the first drift chamber they are then brought into the second drift chamber for confirmation.

The second phenomenon mentioned above (undefined ion mobility peak shifting through explosives detection window causing false positives) can be caused by clusters of ions and neutral molecules in the drift region. In conventional IMS, counter current drift flow designs have been used to reduce this effect, however, because of the space limitations in conventional IMS designs, neutral reactive molecules are not completely removed from the drift region. In a one method of operation of a MDIMS according to the present invention, the drift flow is set such that substantially no un-ionized sample is introduced into the drift chambers.

The third phenomenon (high chemical background noise from contaminants causing false negatives in explosive detection) represents another fundamental issue with current IMS-based detection systems. It can be caused by competition for charges in the ionization source; for example, interferants can reduce ionization efficiency of the sample and therefore reduce detection sensitivity. With current IMS-based trace detection systems, the thresholds of explosive detection windows are set with consideration of this masking effect. With higher resolution of various embodiments of the MDIMS systems and methods of operation of the present invention, the alarm thresholds can be set to a lower level.

In various embodiments of the present invention, a CFDI mode of operation of the MDIMS is used to achieve pre-separation of chemical species that have different charge affinities in a sub-second time frame. Accordingly, in acquired 2-D ion mobility profile, interferants/masking agents with charge affinities that are different from explosives will locate at different positions in the profile, and such becomes part of the differentiation and identification process.

Further Details of MDIMS Apparatus and Methods of Operation

Referring to FIG. 4, provided is a schematic drawings of various embodiments of a multi-dimensional ion mobility spectrometer having dual second ion mobility dimensions. FIG. 4A is a front cross section view and FIG. 4B is a side cross sectional view of the MDIMS.

In various embodiments, a MDIMS comprises an ionization source 401 to, for example, (a) generate reactant ions and a reaction region where reactant ions can react with samples and form product ions to be detected for sample identification; (b) generate sample ions for detection, (c) or both. The reaction region can be guarded by ion guides 402 that generate a substantially continuous electric field to, e.g., lead the ions to the first dimension drift region 417 (first drift tube).

Multiple Step Separation (MSS) Mode

In MSS mode operation, a pulse of ions are generated by opening an ion gate 403, to introduce them into the first dimension drift region 417; the ions are separated based on their mobilities under the guidance a substantially continuous electric drift field in the first drift tube 417. In one embodiment, the electric field is generated by a series of ion guides 404. Each ion guide can comprise one or more electrodes; and different voltages can be applied on each electrode to establish the potential difference across the first drift tube. For example, FIG. 4B shows four electrodes used for each first dimension ion guides.

In various embodiments of MSS mode operation, as a first group of ions reaches the first dimension detector matrix 405, a kick out voltage can be applied to generate a high electric field that is perpendicular to the first dimension drift field, thus the ions separated in the first dimension are moved into the second dimension drift region 418. An electric field separator screen 406 can be used to help define the electric field in the second dimension. Ions introduced into the second field will continue to drift across the second dimension drift region 418 and further separation can be achieved. The ion guides 407 in the second dimension 418 can be arranged similarly to the first dimension ion guides 404, for example, if a third dimension of separation is desired. If a third dimension is desired, complete square electrodes can be used as the ion guides. Ions separated in the second dimension can be detected by the detector 408. The detector can comprise multiple detectors according to required special resolution of the spectrometer or a single detector.

In various embodiments, a partial kick out operation can be performed when ions are introduced from the first dimension to the second dimension. If only a portion of the ions are kicked out, the mobility measurement in the first dimension can be resumed after the kick out. Thus, an ion mobility spectrum can also be acquired independently in the first dimension. As a complete kick out can increase the sensitivity in the second dimension, alternating between these operation methods can be beneficial. In addition, a clean up operation, e.g., remove all ions in the drift chambers by an applied "kick out" electric field for an extended period of time, can also be added between detection cycles.

The low dimension operation of the spectrometer can be used as fast screening method to generate a quick survey of the ionic species from the ionization source. In combination with the normal operation of the MSS mode, the survey of the ionic species can be used as an index to guide upper dimension operations. The survey mode operation can also be used to selectively kick out ions of interests, simplify higher dimension spectra, and save total analysis.

Different drift/separation conditions can be established independently for each dimension, e.g., different drift gases may be used in each dimension or different drift gas temperatures in each dimension.

The MDIMS can be operated in a fashion where a number of multiple dimensional positive ion mobility data is collected followed by a number of multiple dimensional negative ion mobility data. The sequence can be realized, e.g., by alternation the polarities of electric fields in the spectrometer.

FIG. 5 shows the simulation results of electric field arrangement inside a MDIMS substantially similar to that of FIGS. 4A-4B. FIG. 5A shows two perpendicular electric fields 502 and 504 can be arranged in the MDIMS. In FIGS. 5B and 5C, two half square ion guides 508 and 510 are simulated as an example. FIG. 5B shows side view of first dimension drift region. While ions are drifting down in this region, both half-square electrodes 508 and 510 are set at the same voltage; thus, there is substantially no electric field perpendicular to the drift field. Referring to FIG. 5C when ions in the first dimension are kicked out into the second dimension, different voltages are applied on the half square ion guides 508 and 510 creating a kick out field 506. In this particular simulation, the upper half square ion guides 510 are at 1,000 V lower potential than the lower half-square ion guides 508. The kick out operation can be achieved, for example, in the microsecond to seconds range.

During MSS mode operation, the directions of the drift gas flow can be set to be counter to or across from the ion movement. For example, in various embodiments, gas port 413 can be used as the second dimension drift gas inlet and port 412 as the first dimension drift gas inlet, port 409 as the sample flow inlet and port 410 as purge gas outlet. The other ports are preferably plugged or remove when they are not in use. The size of each port can be selected depending on the flow required to achieve the flow pattern inside the spectrometer and preferably the drift flow sweeps the entire drift region and removes excessive sample molecules and any other reactive neutral molecules.

In various embodiments, the drift gas can be supplied to the higher dimension in the direction that is in substantially parallel to the lower dimension. For example, port 415 can be used as the second dimension drift gas inlet, port 414 as the second dimension drift gas outlet, port 412 as first dimension drift gas inlet, and port 410 as the first dimension drift gas outlet. Under linear flow conditions and the parallel flow pattern, for example, limited mixing of drift gas near the dimension interface is expected.

Storage and Burst Analysis (SBA) Mode

In SBA mode operation, the sample is provided into the spectrometer through port 409. Through the ionization source 401, the ionized the samples are brought into the first dimension drift region 418 by gas flow. In case where only a single polarity of ions is of interests, the flow can be purged from port 412 or port 411. In various embodiments of the SBA operational mode, the first dimension drift tube can be used as ion storage device to, e.g., increase the duty cycle of the device.

In various embodiments, where both positive and negative ions are of interest, a Dual Polarity Ion Extraction (DPIE) method can be used. FIGS. 5A and 5B shows the electric field generated during ion storage and DPIE operation. For example, FIG. 5C shows that three walls in the first dimension (left, bottom, and right) are at 1000 V and gate grid are set at 0 V and 2000 V, respectively. The electric field distribution shown in FIG. 5B illustrates that the gas flow is used as the force to carry ions through the first dimension 502, where the electric field in the first region 418, 502 is set to substantially zero until a kick out pulse is generated. In the case of using port 412 as the sample flow exit, when electric fields in both the reaction region 416 and the first drift region 418 are removed; the sample ions will only be carried across the first dimension by gas flow. In various embodiments, when the detector 405 detects a sufficient ion current level, a complete kick out toward the second dimension 420, 504 is be performed. In a continuous sample source detection scenario, the sequence is repeated.

Selective Higher Dimension Ion Monitoring Mode

In various embodiments, selectively monitoring ion current at a specific electrode of higher dimension detector matrix can improve system selectivity by eliminating uninterested ions on other electrodes in the same detector matrix. The ion mobility profile can be constructed using this selective monitoring method with signals from a plurality of electrodes. In various embodiments, selectively monitoring ion current at a specific electrode of higher dimension detector matrix can improve system selectivity by eliminating uninterested ions on other electrodes in the same detector matrix.

In various embodiments, of the MDIMS, the higher dimension drift chamber may have a reduced length. In these embodiments, the device is simplified. The ion mobility based separation achieved in the lower dimension and detected on the higher dimension detector matrix with further separation in the higher dimensions. For example, ion can be separated in first and second dimensions, and then they are detected on third dimension detector matrix without further separation in the third dimension. In this case, the "kick out" timing is controlled to move ions into higher dimension with optimal ion mobility resolution and ion population to maximize the system performance Continuous First Dimension Ionization (CFDI) Mode In various embodiments of CFDI mode operation, the samples are introduced to the spectrometer from port 412 as pulses of gas. The sample gas pulse can be formed in a wide variety of ways, for example, by thermally desorbing chemicals from a surface, as the eluent of a chromatographic separation, by pumping the sample into the spectrometer for a short period of time, introduction through a pulsed valve, etc. In many embodiments, the flow under a linear flow condition, and a "plug" of gas phase sample is directed from the port 412 towards the ionization source 401 by gas flow. Pulses of reactant ions (preferably at high density) are generated by the ionization source 401 and guided by the electrical drift field to drift towards the sample "plug". As the pulse of reactant ions and samples intercept in the first dimension 417, a portion of the samples are ionized. As the sample encounters multiple reactant ion pulses in the same acquisition period, chemicals in the sample "plug" are ionized. Chemicals with different properties (e.g., charge affinity) can thus be separated and detected at different locations on the detector matrix 408. This gas phase titration method can improve ionization efficiency of ion mixture where chemicals with different properties coexist. By this means chemicals that can not be detected in conventional IMS can be detected.

Referring to FIGS. 3A-D, a schematic representation of the CFDI process is illustrated in a drift region 302. A gas phase sample 304 is pulsed into a drift tube 302 at a first time and conveyed in a first direction 305 along at least a portion of the drift tube, wherein the first direction is substantially parallel to the direction of carrier gas flow in the drift tube. The speed of the carrier gas flow and gas phase sample is equal or greater than zero cm/second. A plurality of pulses of reactant ions 306 are also introduced into the drift tube 302 at predetermined times relative to the first time and conveying by the electrical drift field in a second direction 307 along the drift axis 308, wherein the second direction 307 is substantially anti-parallel to the direction of carrier gas flow 305 in the drift tube. The gas sample 304 interacts with a first group of reactant ions 310 (comprising one or more of the plurality of pulses of reactant ions) to ionize a chemical species in the gas phase sample pulse 304 and produce a first ionized chemical species 314. In various embodiments, a kick out field is applied (e.g., by application of a kick out voltage to an electrode set 318, 320 and 322) to move the ions 314 in a direction 316 out of the drift tube and into another drift dimension. In various embodiments, the process repeats for other groups of ions 311, 312, that interact with the gas sample 304 to produced further ionic chemical species.

In various embodiments, the CFDI can also be performed in the reaction region 416, shown in FIG. 4. A plurality of pulses of reactant ion is generated by pulsing ion gate 419 while pulsed sample are introduce to the spectrometer from gas port 410. In this implementation, ion gate 403 is removed or kept open. Pulse of ions generated in the reaction region 416 are separated in first dimension drift region 417, and then the separated ions are extracted in higher dimension drift region 418 for further ion mobility analysis if so desired. In various embodiments, the CFDI method can be used as an independent ionization source directly interfaced to spectrometers, such as differential mobility spectrometer, ion mobility spectrometer or a mass spectrometer, either inline or perpendicular to the direction drift electric field. In embodiments where CFDI is used for a single IMS, the shutter grid 419 will be used instead of grid 403. The ionized chemical species continue to drift in drift region 417 after formation in the reaction region 416. Similarly, interfaces to other spectrometers, such as differential ion mobility spectrometers and mass spectrometers, can also be realized by placing the sample inlet of these instruments directly after the reaction region.

The CFDI mode can be preformed using reactant ions with different chemical properties. For example, modifying the ion chemistry using a variety of chemical reagents that react with initial reactant ions can generates reactant ions with different chemical properties. These ionic species can be used, e.g., to ionize samples introduced to the spectrometer. Similar effects can be achieved, e.g., by using an ionization source that can generate different ionic species or charged particles/droplets. In various embodiments, altering the ionization chemistry can be used to achieve substantially selective ionization of targeted chemicals in the sample. For example, a series of ion pulse with different chemical properties can be used to ionize chemicals with compatible ionization properties in the sample.

Selective Ion Introduction (SII) and IMS" modes

In Selective Ion Introduction (SII) mode operation, one or multiple groups of selected ions are kicked out into a higher dimension. The selective kick out can be realized by applying a kick out voltage at a predetermined time to the region where ions of interests are traveling through at a given timing. In various embodiments, the kick out pulse is not necessarily applied to a selected region of the lower dimension, but the higher dimension drift chamber does not intercept the lower dimension only over a portion of length of the lower dimension; thus, e.g., a selected location can be designed only to allow a small group of ions to be kick out into the second dimension. A similar result as described with respect to MSS mode can be achieved by controlling the kick out timing and performing multiple acquisition cycles.

In various embodiments, the SII mode can be effective in resolving ions in a narrow drift time range. For example, suppose a first drift dimension is used as a screen scan, and a compound of interest (e.g., TNT) is detected as potentially present. To further confirm that ion responded in the detection window (time window) is the compound of interest, one can selectively kick out the peak in that detection widow into the second dimension for further separation. From the second dimension, ions that fall into a selected window can be kicked out into a third dimension. This process can be repeated until the ion current is exhausted if so desired.

Multiple Drift Chamber Condition

In the various methods and operational modes, each drift chamber is operated under independent and/or different drift conditions. These conditions include, but are not limited to, different kinds of drift gases, drift gases with different chemical modifiers, different temperatures, different pressures, different electric field strength, different flow rate, different phases of drift media, and directions, etc. In various embodiments, the purpose of changing the conditions is to achieve separations of the ionic species using their unique chemical and/or physical properties and how these can change with drift condition and thus can result in mobility changes in the spectrometer. For example, ion mobility measurements using different drift gas have demonstrated that ions with different properties can have different drift time in the sample spectrometer (See, for example (1) William F. Siems, Ching Wu, Edward E. Tarver, and Herbert H. Hill, Jr., P. R. Larsen and D. G. McMinn, "Measuring the Resolving Power of Ion Mobility Spectrometers", Analytical Chemistry, 66, 1994, 4195-4201; (2) Ching Wu, William F. Siems, G. Reid Asbury and Herbert H. Hill, Jr., "Electrospray Ionization High Resolution Ion Mobility Spectrometry/Mass Spectrometry", Analytical Chemistry, 70, 1998, 4929-4938; (3) Ching Wu, Wes E. Steiner, Pete S. Tornatore, Laura M. Matz, William F. Siems, David A. Atkinson and Herbert H. Hill, Jr., "Construction and Characterization of a High-Flow, High-Resolution Ion Mobility Spectrometer for Detection of Explosives after Personnel Portal Sampling" Talanta, 57, 2002, 123-134; and (4) G. Reid Asbury and Herbert H. Hill, "Using Different Drift Gases to Change Separation Factors ($\alpha$) in Ion Mobility Spectrometry", Analytical Chemistry, 72, 2000, 580-584; the entire contents of all of which are hereby incorporated by reference).

In various embodiments of MDIMS systems, the higher dimension drift region, such as the second dimension region, can be operated in different phases of drift media, e.g. gas or liquid. The liquid phase drift cell can be constructed with two parallel plates or grids instead of a conventional drift tube design. The liquid phase drift cell can be a thin layer of liquid that has an electric field across the layer. The higher order dimension drift cell has drift axis that is substantially parallel or substantially perpendicular to the first dimension drift axis. The higher dimension drift cell has multiple compartments (channels) that are substantially perpendicular to the lower dimension drift axis. The higher dimension drift cell can be used for selectively collecting samples separated in the lower dimension drift tube. The higher dimension drift cell can be further interface to other separation and detection apparatus, including but not limited to electrophoresis, chromatography, UV absorption and other spectroscopic apparatus.

In various embodiments of MDIMS systems of the present inventions, different drift gases are used in different drift tubes and/or dimensions of the MDIMS to separate ionic species in a higher dimension (e.g., a second dimension) that are not sufficiently separated in the drift gas in a lower dimension (e.g., the first dimension). It is to be understood that the drift gas can be a mixture of two or more gases. Similar separations can also be done by varying other drift chamber conditions.

Further Examples of MDIMS Configurations

Figure 7:
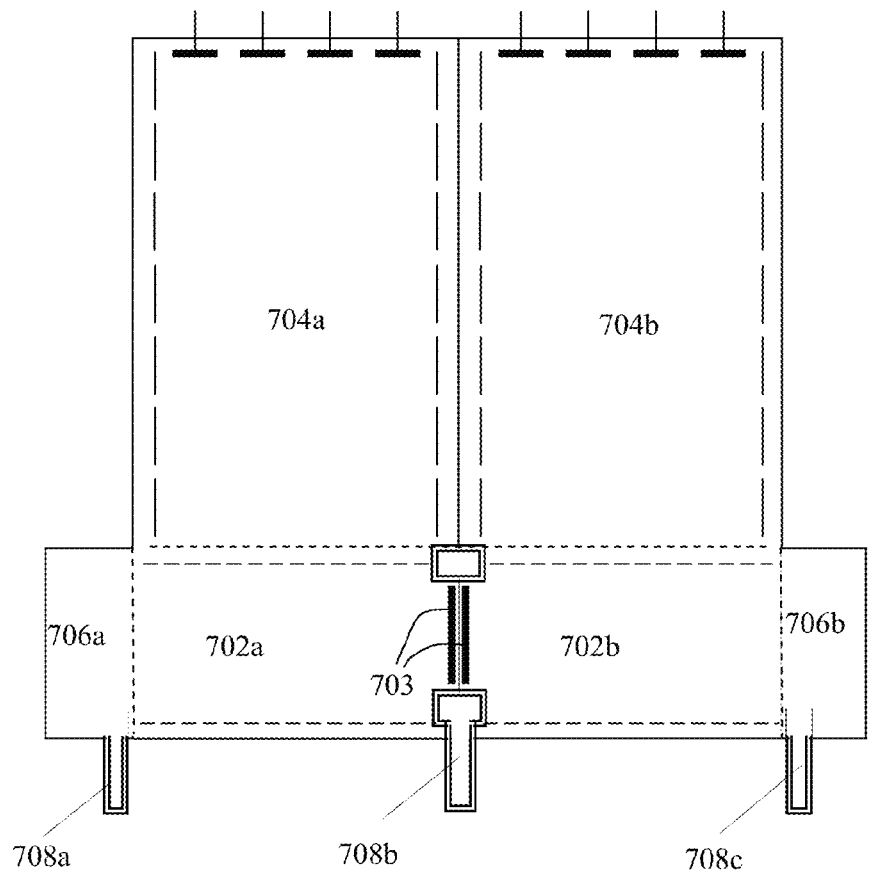
FIG. 7 is schematic drawing of various embodiments of a DSDIMS with multiple second dimensions in parallel position and multiple ionization sources.

FIG. 7 shows various embodiments of a MDIMS where multiple higher dimensions drift chambers 704a, 704b are arranged in substantially parallel and multiple ionization sources 706a, 706b are used, for example, to generate ions in both positive and negative polarity. For example using a the CFDI mode of operation, a sample can be introduced to the spectrometer from the port 708b in the center of the first dimension; two ionization sources of different polarity can be used to generate high density reactant ions that are guided into the first dimension chamber 702a, 702b by an electric field that moves the reactant ions toward the center of the first dimension. Where an electrospray ionization source is used, for example, charged droplets can be used for ionizing the sample using the secondary electrospray ionization principle. The ionized chemicals are brought into the higher dimensions 704a, 704b for mobility measurements. This embodiment can be used, for example, to analyze the same sample using different ionization sources using different ionization modes and'/or drift conditions as described above for example. For example, the device can have more than two first dimension reaction chambers and higher dimension drift chamber combinations to utilize more ionization methods. The higher dimensions can be operated in single or dual polarity mode (e.g., DPIE) to extract ions from the first dimension.

Figure 8:
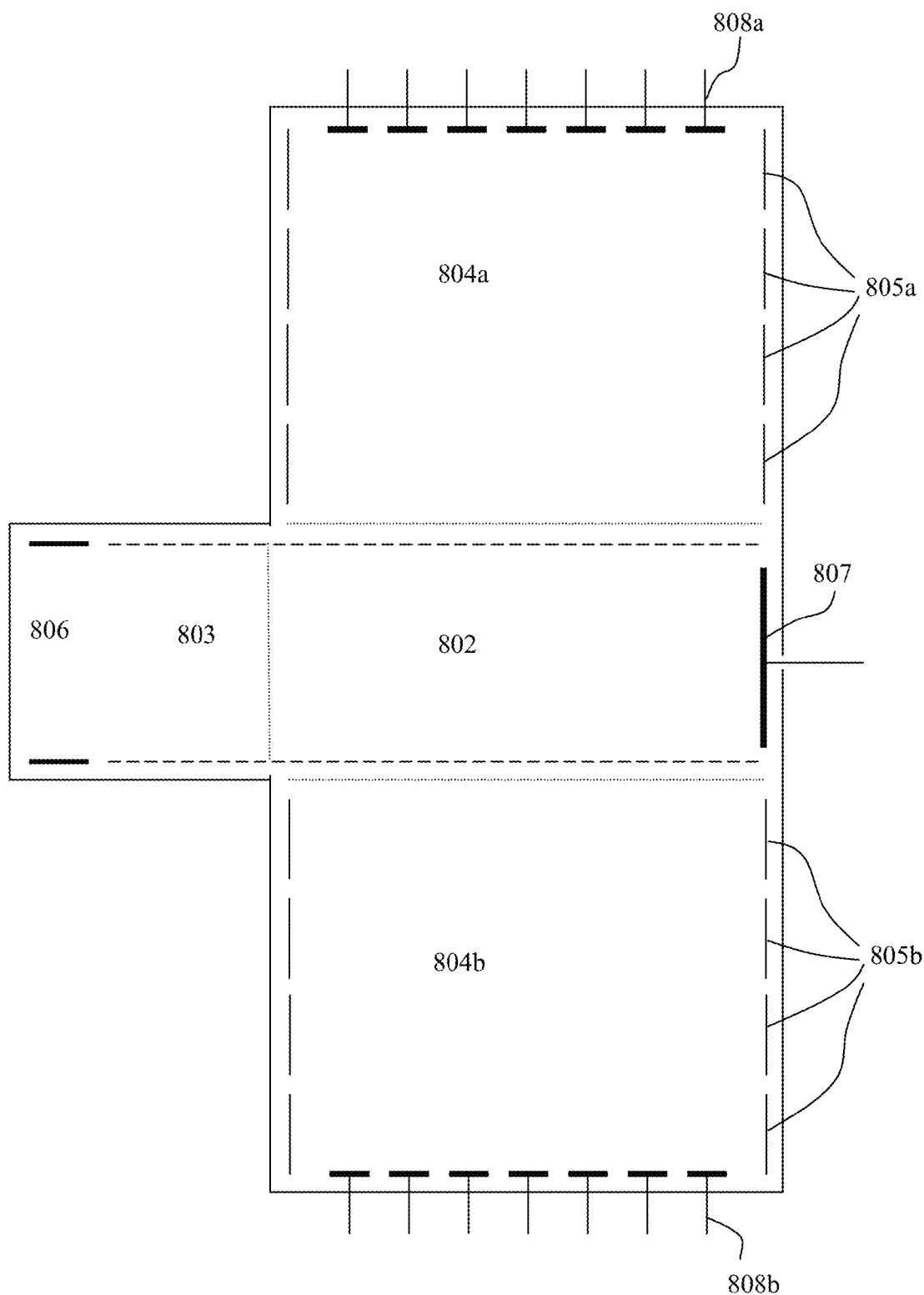
FIG. 8 is schematic drawing of various embodiments of a DSDIMS with multiple dimensions in an opposing position.

FIG. 8 is a schematic drawing of various embodiments of a MDIMS with a higher dimension 804a, 804b extending in opposite directions from a lower dimension 802. The second dimensions can be operated in single or dual polarity mode as previously described. The first dimension can be operated, for example, as an ion flow cell for ion storage. This configuration can be utilized, for example, such that ions with different polarities can be kicked out into the opposite higher dimension drift chambers when it is operated under a SBA mode. In various embodiments where the higher dimension drift chambers are dual mode chambers, the DPIE method can be used, e.g., to deliver ions to both dual mode chambers for independent analysis where the dual mode drift chambers can be operated under different drift conditions.

Figure 9:
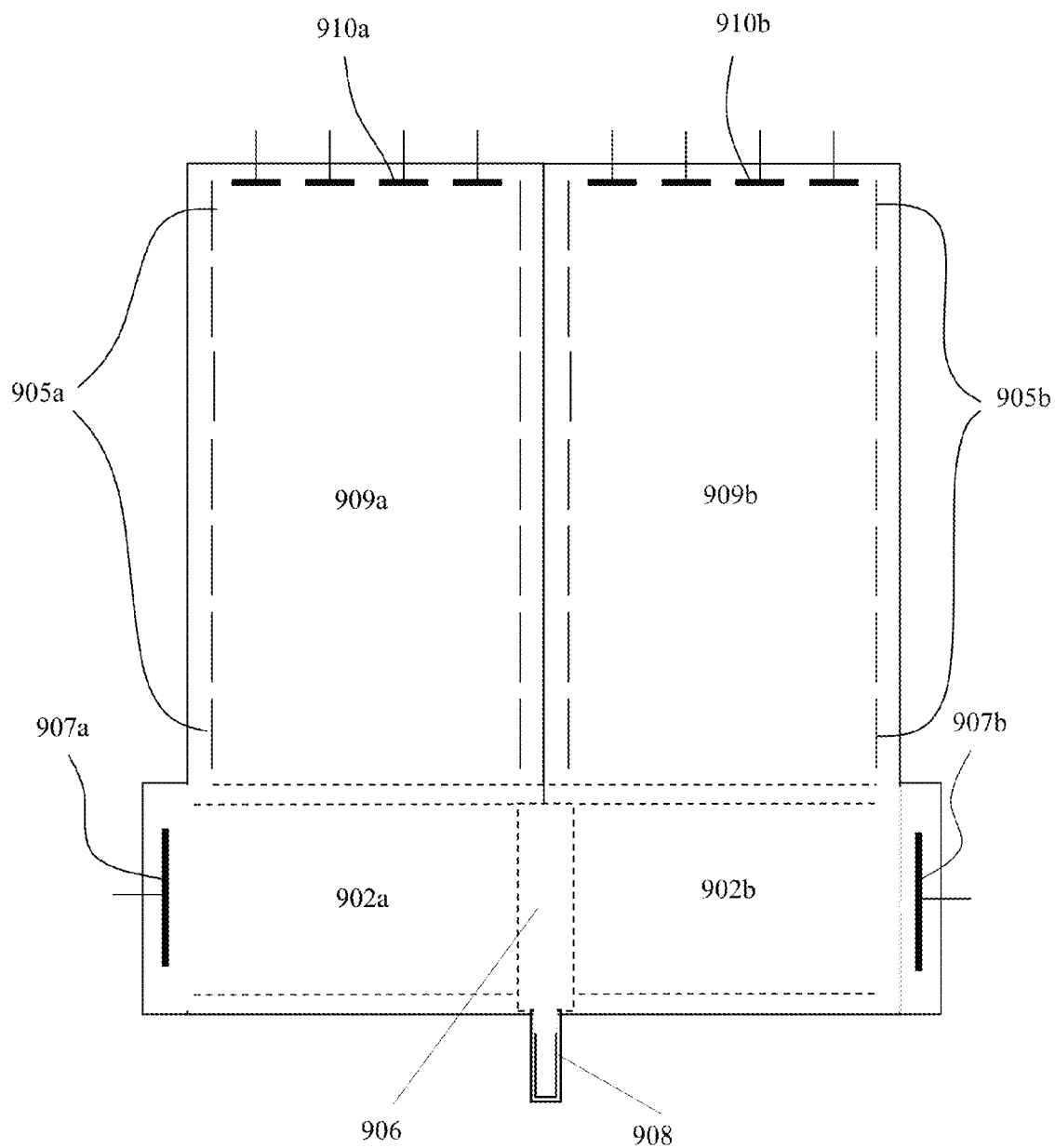
FIG. 9 is schematic drawing of various embodiments of a DSDIMS with a single sample source and multiple first dimension chambers; which can be used, for example, with different polarities.

FIG. 9 is a schematic drawing of various embodiments of a MDIMS with ionization source 906 and sample inlet 908 between the inlets to the drift tubes of a second dimension 909a, 909b. Ions formed in this ionization source 906, e.g., can be extracted into two different sections of the first dimension 902a, 902b. Each section can be operated in either positive or negative polarity mode. For example, in various embodiments each section of the first dimension of the MDIMS is used as a first dimension drift chamber. Each section of the first dimension can have its own higher dimension drift chamber for further ion separation.

Figure 10:
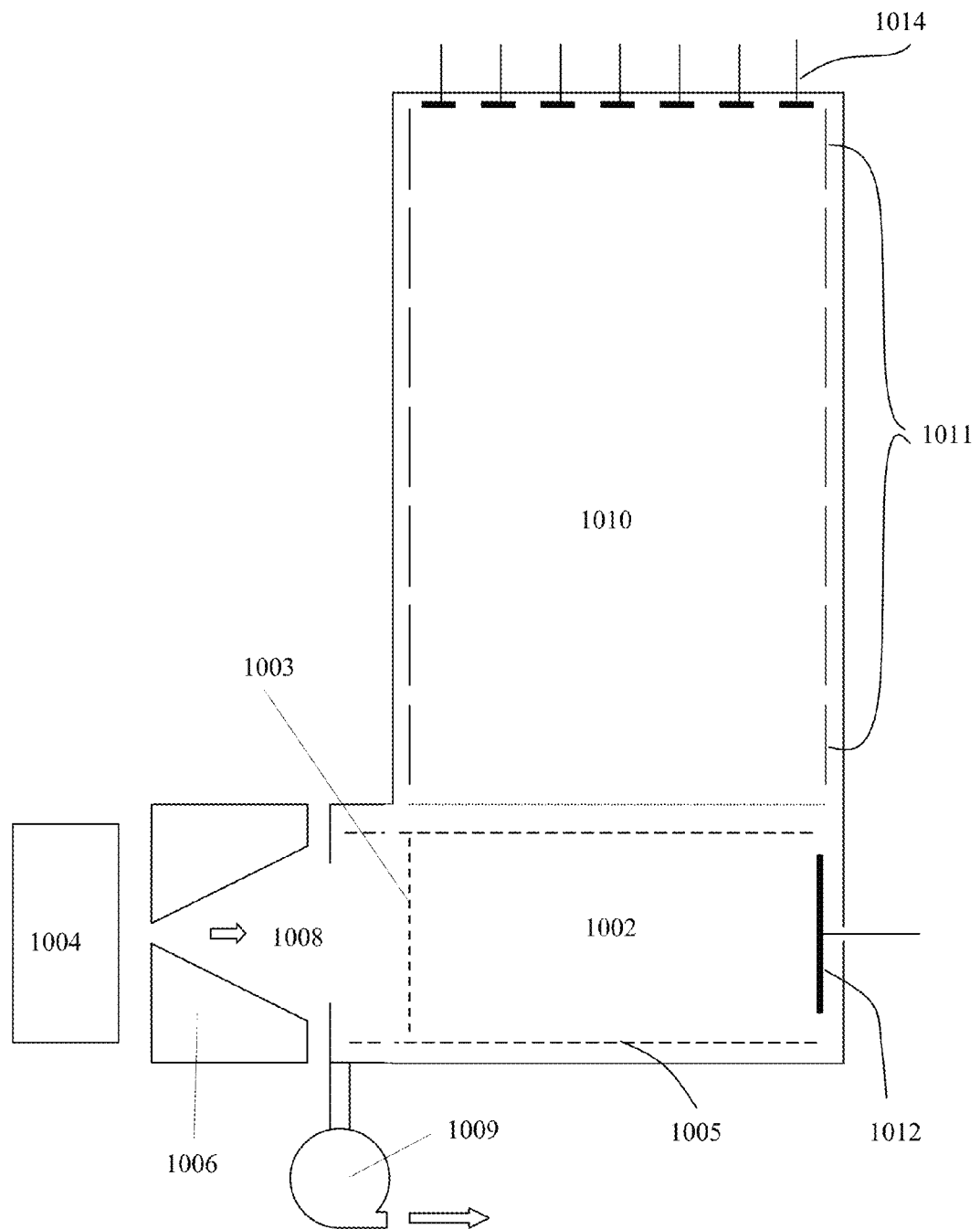
FIG. 10 is schematic drawing of various embodiments of a MDIMS for sampling chemicals in ionic form and/or from an external ionization source.

FIG. 10 schematically depicts various embodiments of an MDIMS of the present inventions for sampling chemicals in ionic form or from an external ionization source. Such embodiments include a source 1004 in fluid communication with a first drift tube 1002 through an interface 1006. The methods of the present inventions that operate on ions and operational modes described herein can used with such embodiments. This embodiment eliminates the necessity of internal ionization source and reaction region of the IMS system. The ionized chemicals are either brought into the interface 1006 by an electric field (in this example, the ionization source 1004 and interface 1006 are set at different potentials), or by gas flow (in this example, the ionic species 1008 are moved into interface 1006 by sampling pump 1009. Once the sample ions 1008 are moved in to the interface 1006, they are pulsed into the first drift dimension 1002 through ion gate 1003. They are either detected on first ion detector 1012 or subsequently kicked out into the second dimension drift region 1010 and detected on detectors 1014, under guidance of ion guides 1005 and 1011, respectively.

IMS$^n$ and Hyphenate Systems

Figure 11B:
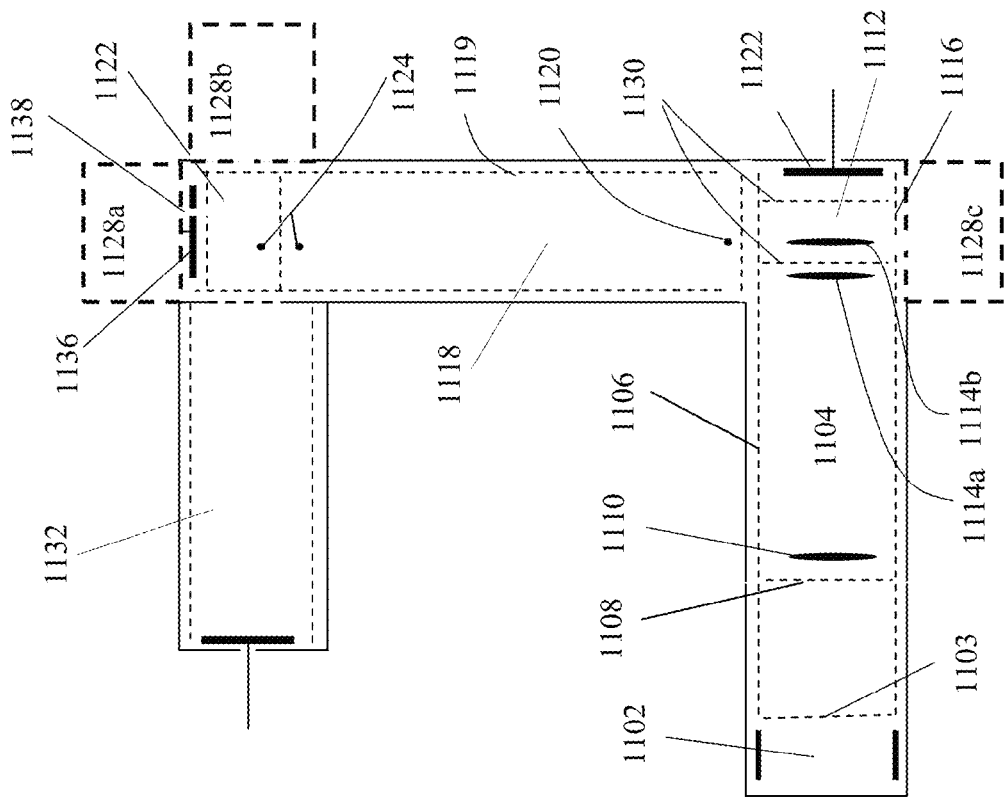
FIGS. 11A and 11B are schematic drawing of various embodiments of a MDIMS useful, for example, for SII and MS" implementation.
Figure 11A:
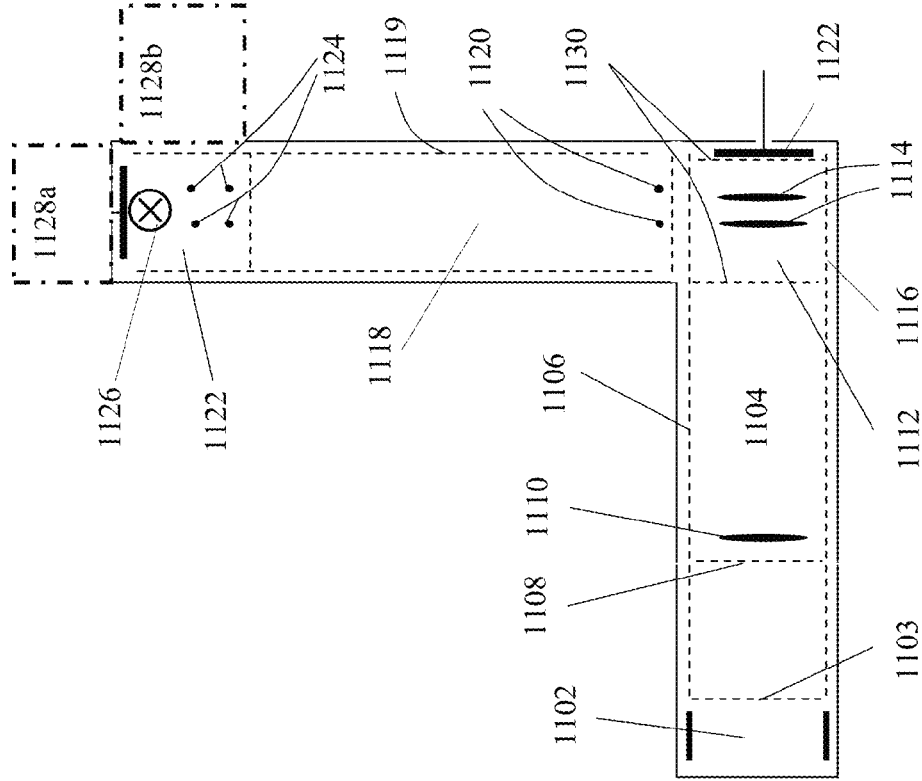

FIGS. 11A and 11B show schematic examples of various embodiments that can be used to realize the SII mode operation with IMSn. By reducing the physical size of the higher dimensions and controlling the timing of the kick out pulse, a selected group of ions 1114 that drifted into the kick out region 1112 can be brought into a higher dimension drift chamber 1118 where they can be further separated. The same process can be continued until the nth separation performed in different drift chambers. The geometry of the interconnected drift chambers can be two dimensional (FIG. 11B) or three dimensional (FIG. 11A), thus the number of times a higher order mobility separation can be conducted is not necessarily limited by the physical space available for the spectrometer.

In various embodiments, FIG. 11A shows schematic of a three dimensional MDIMS that illustrate SII mode operation. When gas phase sample is introduced into the reaction region of the first dimension drift tube, between ion gates 1103 and 1108, the sample is ionized by either CFDI or conventional ionization methods with reactant ions created by ionization source 1102. The sample ions mixed with reactant ions are pulsed into the first drift region 1104. Under the guidance of the electric field generated by ion guide 1106, the ion mixture separates in the first dimension. At a predetermined timing when ions of interest 1114 drift into the kick out region 1112, a kick out voltage can be applied to a set of electrodes (including spited ion guide 1116 and grids 1130) to extract ions into the second dimension. As ions 1114 are compressed in the interface between the kick out region 1112 and second dimension drift region 1118, narrow pulses of plural separated ions 1120 are created at the beginning of second dimension drift region 1118. The ions pulses 1120 are separated in the drift region 1118 that is guarded by ion guides 1119. The further separated ions 1124 are extracted from second ion kick out region 1122 into the third drift chamber that has a drift direction 1126 (pointing insider the paper) that is orthogonal to the first and second dimension. The extracted ions repeat the process described above in the third dimension or higher.

In various embodiments, FIG. 11B shows schematic a MDIMS operating in SII mode with a two dimensional structure. FIG. 11B illustrates that one peak 1114b isolated by the first dimension drift tube is extracted into second dimension, and then one peak isolated by the second dimension drift tube is extracted into the third dimension 1132 having a drift direction that is substantially perpendicular to the second dimension and substantially anti-parallel to the first dimension. In this example, the drift axes of all dimensions are on the same plane.

For example, in various embodiments, the configuration of FIGS. 11A and 11B can be interfaced to other detectors, such as a mass spectrometer. IMS-MS systems are commonly used to achieve mobility based separation before mass analysis. The interface to a mass spectrometer can be in-line with ion drifting direction behind the detector matrix, e.g. 1122 or 1136. FIG. 11B shows an interface to a mass spectrometer 1128a through an opening on the second dimension detector matrix 1138, or perpendicular to the drifting direction using a kick out pulse to push ions into the interface 1128b and 1128c. Higher ion transportation efficiency is expected in the later case.

Sampling Apparatus

Samples can be introduced to the MDIMS either as a pulse in the flow stream, continuously, or combinations thereof. The pulsed sampling method can be used in several operational modes. A thermal desorption chamber in the front of the spectrometer can be used to provide samples. For example, for samples from a swab a desorption chamber can continuously heat up the swab and then pump high concentration chemical vapor into the MDIMS. A valve can be used to control the amount of sample allowed to enter the spectrometer. Depending on the operational modes described above, sample may be allowed to continuously flow into the MDIMS with an ionization source. The desorption chamber can contain adsorbent materials for a sample pre-concentration step of operation. For example, as a low concentration or complex mixture sample is introduced to the chamber, adsorbent can selectively trap compounds of interests and then desorb them into the MDIMS.

Sample Swabs

There are numerous ways to improve sampling efficiency. In various embodiments, "wet" sample swabs can be used to facilitate complete sample collection instead of dry swabs. The wet swabs can assist the collection efficiency by increasing the contact between swab and surface, and provide better physical pick-up of sample. By selecting an appropriate solvent mixture, the targeted explosive can also dissolve into the swab, thus achieving higher sampling efficiency. To facilitate wet swabbing operation a matching sample swab and desorber design can be used.

The swab is preferably designed with a pattern of hydrophobic and hydrophilic surfaces for the designated solvent or solvents to be used. This pattern can match, e.g., the pattern of the heater inside of the desorber. In a practical search scenario, the dry and wet sample swabs are often used depending upon the sampling surface. Since the wet swab has higher collection efficiency, it could be used, e.g., for confirmative tests to resolve an alarm from a dry swab; it could be used in a "complete wipe operation" to collect low level explosives particles, etc. Since the explosives can be soaked into or adhere to the sample swab, it could also be used to reserve samples as evidence Air Sampling In various embodiments, the MDIMS systems of the present inventions can be operated with continuous sampling of vapor in surrounding environments. The sample frequency can be preset to serve the purpose for either early warning of, e.g., a high quantity of explosives or other safety concerns. Common volatile explosives, such as nitroglycerine, TATP or even explosive Taggants, can be detected from the vapor phase. Thus, in various embodiments the MDIMS systems of the present inventions can be used for "sniffing".

Sample Concentration

In various embodiments, the sampling capability and/or desorption efficiency can be enhanced by using a pattern of high chemical affinity compounds, chemical resistive surfaces, or both on the inner wall of the desorption chamber. The high chemical affinity compound coated surface can be used to preconcentrate vapor in the gas phase and/or selectively trapping target compounds in the presence of other chemicals, such as solvents used for wet sampling. The heating element for the desorbed parts can be arranged, e.g., to heat up the area where the high chemical affinity coat is applied. Such a selective heating approach can be used, e.g., to reduce the heat used for desorption, and thus reduced the total power consumption of the detection system.

Sample Ionization

The MDIMS systems of the present invention can comprise one or more ionization sources. The ionization sources can be used to generate reactant ions, directly ionize targeted chemicals, or both. Suitable sources include, but not limited to, radioactive ionization, electrospray ionization, desorption electrospray ionization, surface ionization, and corona discharge ionization sources.

Electrospray ionization is one of the preferred sources for inorganic explosives detection. ESI-MDIMS can be used, e.g., to detect chloride based explosives, as well as black powers with high confidence. With a wet sampling scheme, e.g., electrospray ionization can be used to process the wet samples by directly spraying collected sample into the MDIMS. One implementation of this method includes having the wet samples put into a sample holder, which has an electrospray needle and electrodes where an electrospray voltage can be applied. As the sample is sealed inside the holder, pressure is applied to the holder/soaked sample swab either directly or indirectly, and the solvents and dissolved sample reach the electrospray needle, and are electrosprayed to form highly charged droplets. The electrospray sample ions can be guided into the MDIMS for analysis. The combination of wet sampling and direct electrospray ionization for the MDIMS can provide, for example, detection capabilities for both inorganic and organic explosives and other chemicals of interest.

Increasing Detection System Usability

Improved system readiness. Although existing IMS-based trace detection systems can typically meet the throughput requirements in an airport operational environment in undemanding situations, the sample throughput is limited when highly contaminated samples are introduced to the system. Accumulation of contaminants in the system can require long bake out times and/or a complex cleaning procedure using organic solvents. Besides cold spots and active surfaces inside the sample transfer portions of the system and detector, a membrane inlet (e.g., as found in both Sabre 4000 and VaporTracer instruments, manufactured and available from Smiths Detection and GE Security, respectively) used to block low molecular weight contaminants and moisture is one of the most common parts that accumulate higher molecular weight contaminants. To eliminate this main source of "memory effect", various embodiments of a MDIMS of the present inventions use a pulsed inlet system.

In various embodiments of the pulsed inlet, the detector is only exposed to the outside world for a short period of time, typically less than about 20 seconds. The valve only opens when the sample reaches the highest concentration in the sampling chamber. The chamber can be flash heated periodically to clean up accumulated chemicals. The pulsed sample inlet operating scheme is compatible with various embodiments of the MDIMS systems of the present inventions and can help control the total amount of moisture introduced into the drift chambers. A humidity sensor can also be made part of the system to provide additional calibration information for system processing.

One of the most common user errors in conventional systems is miscalibration. Preferred systems of the invention offer a self-calibration/self-diagnostic algorithm that can calibrate the system when it is powered on and periodically without requiring operator attention. In various embodiments, the calibrant preferably lasts the life time of the instrument. This feature can further improve system readiness.

The apparatus of the present invention can be constructed as highly portable instruments. As in any analytical device, there is often a tradeoff between the number of operational features and system portability. In various embodiments of the MDIMS designs and operational methods of the present inventions, the total power consumption and detector size can be reduced. A relatively high fraction of power can be allocated to usage to the front end, including sample desorption and effective clean up operations. Low power consumption computer based systems, e.g., on modern PDA design or the like are preferably used as an element of the portable system. In the balance of selecting between portability and usable features, various embodiments of the present inventions provide a MDIMS detection system with reasonable size that is under ten pounds, and possibly even under eight pounds.

Figure 12A:
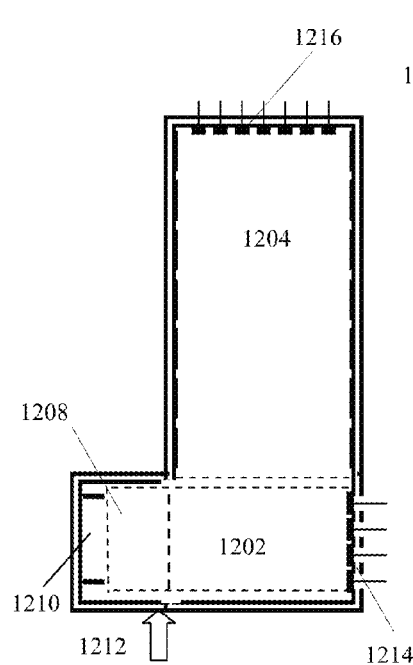
FIGS. 12A-12C illustrative various embodiments of a one MDMS configuration choice for a portable three dimensional instrument according to various embodiments of the present inventions.
Figure 12B:
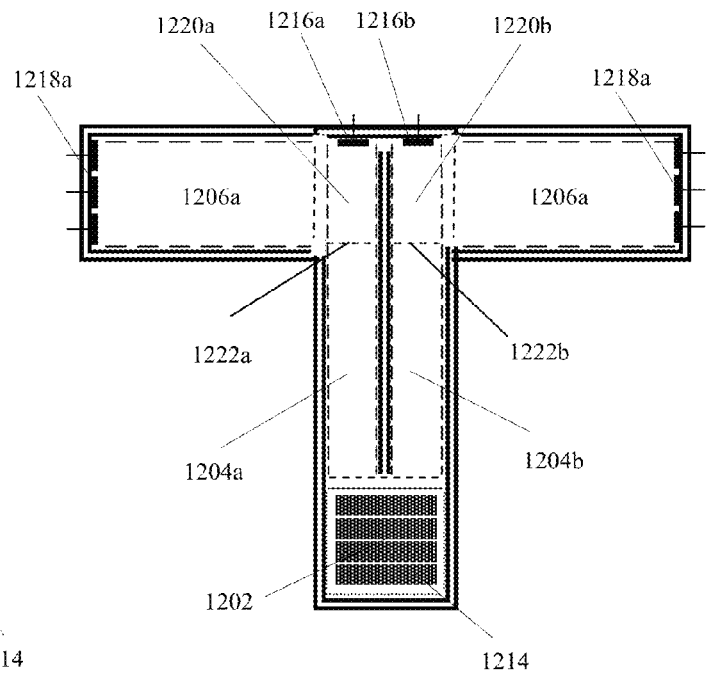
Figure 12C:
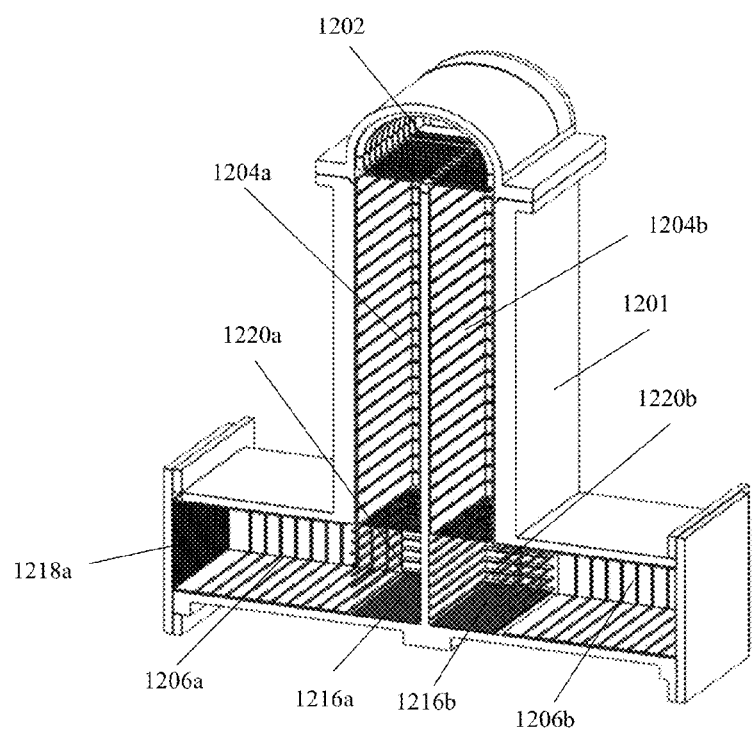

In various embodiments of the MDIMS, FIG. 12A-C shows the schematic of an example of the compact MDIMS. The device is configured with three dimensions, including one first dimension chamber 1202, two second dimension drift chamber 1204a, 1204b, and two third dimension chambers 1206a and 1206b, with a largest dimension of <10 cm. FIG. 12C is the three dimensional drawing of the MDIMS to the scales. The configuration is to realize both CFDI and DPIE with SII mode. In CFDI operation, the reactant ions are formed in ion source 1210 and pulsed into the reaction region 1208 to selectively ionize pulsed sample 1212. Ionized samples are separated in first dimension drift region 1202 and then further separated in higher dimension drift region 1204 and 1206.

Figure 13B:
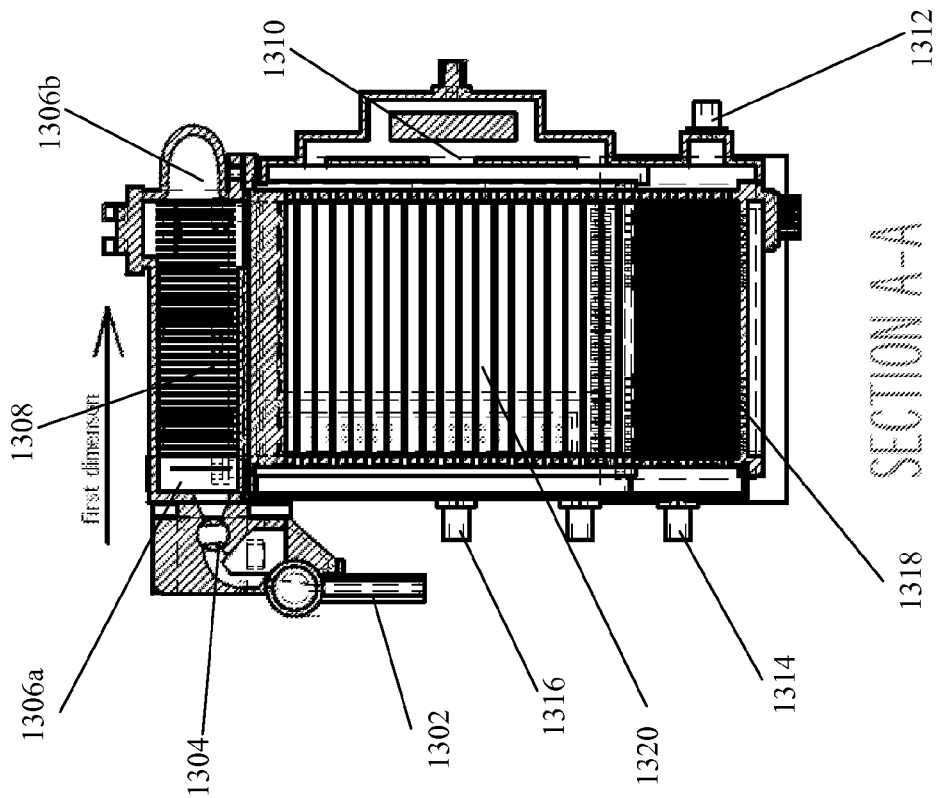
FIGS. 13A and 13B are schematic scale drawings of the MDIMS system of FIGS. 14A-14B.
Figure 13A:
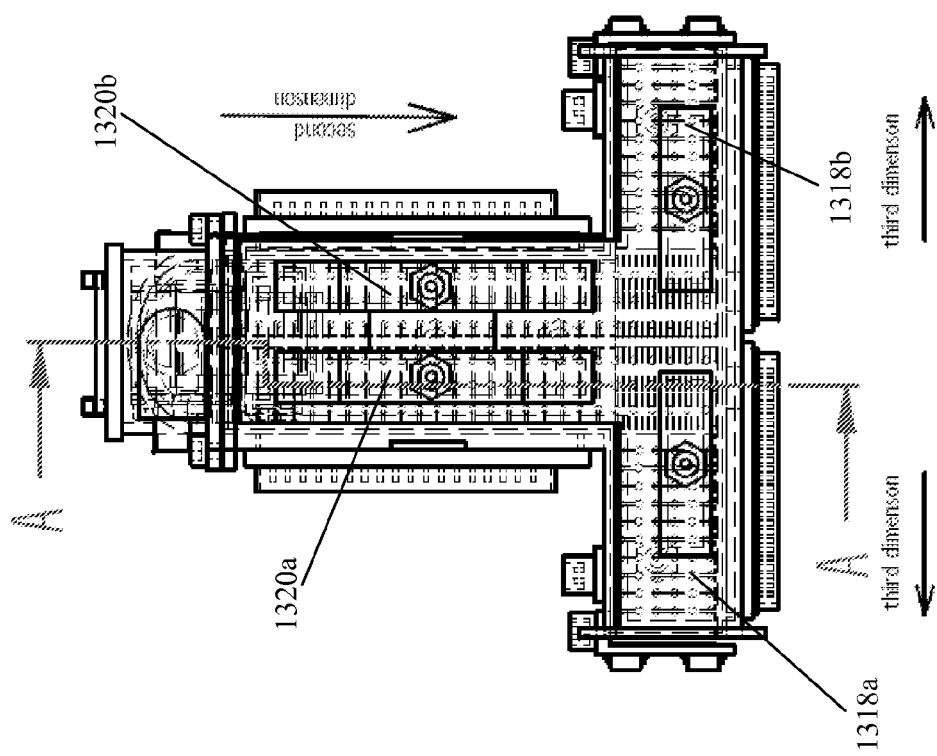

In DPIE operation, both positive and negative ions formed in the ionization source 1210 and reaction region 1208 are carried into the first dimension 1202 by carrier flow without effluence of the electric field. The positive and negative ions are extracted in to the second dimension drift chambers 1204a and 1204b, respectively. The sample ions are detected on the detector matrix in the first dimension 1214, second dimension 1216 or third dimension 1218a and 1218b depending on the instrument usage and it is software controlled. For fast screening operation, ions are detected at lower dimension detectors for high throughput. For highest resolution, ions are measure at the third dimension detectors. The engineering drawings of the configuration are shown in FIGS. 13A and 13B. The practical unit includes sample inlet 1302, sample inlet control valve 1304, ionization source 1306a and 1306b, and first dimension drift region 1308. The drift flow is deigned to sweep cross the second drift region 1320 1320b and third drift region 1318a 1318b. At drift gas inlet 1310 and 1312, a flow distribution system is used to assure even drift flow across the entire drift chambers. The drift gas is purge for port 1314 and 1316.

Figure 14B:
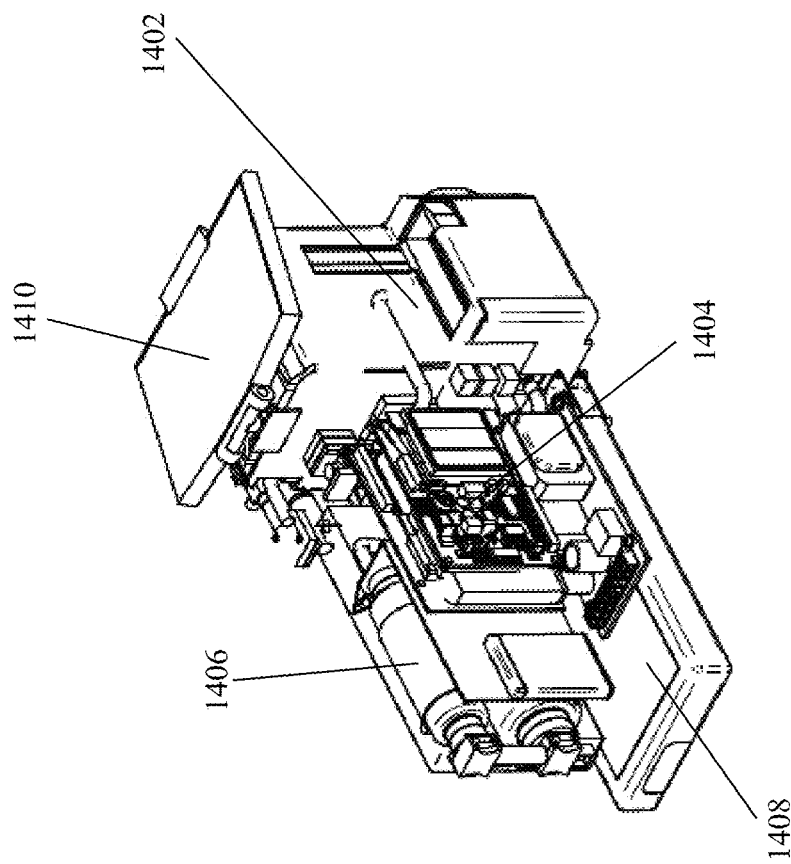
FIGS. 14A-14B are scale schematic drawings of a preferred embodiment of a portable MDIMS incorporating various embodiments of the present inventions.
Figure 14A:
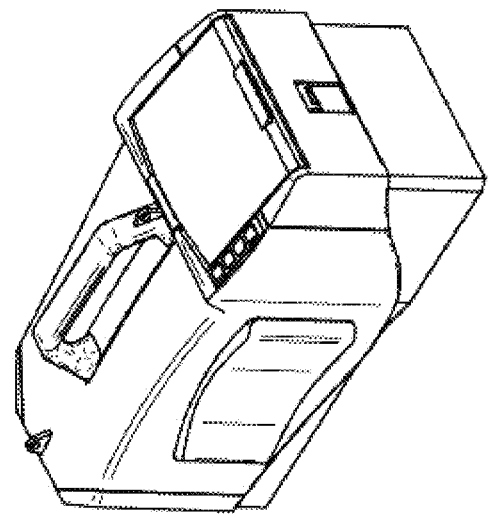

FIGS. 14A and 14B shows engineering drawings of a portable system based on the detector described in FIG. 12 and FIG. 13. The portable package include, pneumatic system 1406, electronics and computer controls 1404, user interface and display 1410, battery power 1408, and a MDIMS 1402.

A modularized design approach is preferably used in the MDIMS of the present inventions to facilitate the provision of future upgrades. For example, a different ionization source may be desired for different applications. Such sources may be, e.g., a corona discharge, electrospray ionization or desorption electrospray ionization. The provision of a modular design can facilitate the changing of the ion source.

In another aspect, the functionality of one or more of the methods described above may be implemented as computer-readable instructions on a general purpose processor or computer. The computer may be separate from, detachable from, or may be integrated into a MDIMS system. The computer-readable instructions may be written in any one of a number of high-level languages, such as, for example, FORTRAN, PASCAL, C, C++, or BASIC. Further, the computer-readable instructions may be written in a script, macro, or functionality embedded in commercially available software, such as EXCEL or VISUAL BASIC. Additionally, the computer-readable instructions could be implemented in an assembly language directed to a microprocessor resident on a computer. For example, the computer-readable instructions could be implemented in Intel 80x86 assembly language, if it were configured to run on an IBM PC or PC clone. In one embodiment, the computer-readable instructions can be embedded on an article of manufacture including, but not limited to, a computer-readable program medium such as, for example, a floppy disk, a hard disk, an optical disk, a magnetic tape, a PROM, an EPROM, or CD-ROM (or any other type of data storage medium).

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

The claims should not be read as limited to the described order or elements unless stated to that effect. While the present inventions have been described in conjunction with various embodiments and examples, it is not intended that the present inventions be limited to such embodiments or examples. On the contrary, the present inventions encompass various alternatives, modifications, and equivalents, as will be appreciated by those of skill in the art.

What is claimed is:

1. A method for detecting samples using a multidimensional ion mobility spectrometric system, the method comprising:
    (a) measuring drift times of ions in a plurality of drift chambers;
    (b) detecting ions of a compound of interest in a first drift chamber;
    (c) conveying a portion of the ions from the compound of interest from the first drift chamber into a second drift chamber; and
    (d) confirming the ions are the compound of interest in the second drift chamber.

2. The method of claim 1, wherein the multidimensional ion mobility profile is two-dimensional or three dimensional.

3. The method of claim 1, wherein the multidimensional ion mobility profile simultaneously identifies ions in both positive and negative polarity.

4. The method of claim 1, wherein the multidimensional ion mobility profile simultaneously identifies ions in a single polarity.

5. The method of claim 1, further comprises ionizing the samples with a CFDI ionization source.

6. The method of claim 1, further comprises confirming the ions are the compound of interest in a higher dimension drift tube, in particular, a third, a fourth, and/or a fifth.

* * * * *